(12) United States Patent
Reuter et al.

(10) Patent No.: US 11,472,770 B2
(45) Date of Patent: Oct. 18, 2022

(54) PROCESS FOR THE PREPARATION OF ENANTIOMERICALLY ENRICHED 3-AMINOPIPERIDINE

(71) Applicant: REUTER CHEMISCHE APPARATEBAU KG, Freiburg (DE)

(72) Inventors: Karl Reuter, Gundelfingen (DE); Tobias Wedel, Karlsruhe (DE); Viktor Meier, Gundelfingen (DE); Mark Kantor, Freiburg (DE); Vasyl Andrushko, Karlsruhe (DE); Florian Stolz, Denzlingen (DE)

(73) Assignee: Reuter Chemische Apparatebau KG

( * ) Notice: Subject to any disclaimer, the term of this patent is extended or adjusted under 35 U.S.C. 154(b) by 0 days.

(21) Appl. No.: 16/579,584

(22) Filed: Sep. 23, 2019

(65) Prior Publication Data
US 2020/0087257 A1 Mar. 19, 2020

Related U.S. Application Data

(62) Division of application No. 14/768,751, filed as application No. PCT/EP2014/053176 on Feb. 19, 2014, now Pat. No. 10,464,898.

(30) Foreign Application Priority Data

Feb. 20, 2013 (EP) .................................... 13156030

(51) Int. Cl.
*C07D 211/56* (2006.01)
*C07D 211/60* (2006.01)

(52) U.S. Cl.
CPC .......... *C07D 211/56* (2013.01); *C07D 211/60* (2013.01)

(58) Field of Classification Search
CPC ............................ C07D 211/56; C07D 211/60
See application file for complete search history.

(56) References Cited

U.S. PATENT DOCUMENTS

| | | |
|---|---|---|
| 5,334,766 A | 8/1994 | Cereghetti et al. |
| 6,942,199 B2 | 9/2005 | Higgs et al. |
| 10,464,898 B2 | 11/2019 | Reuter et al. |
| 2001/0056090 A1 | 12/2001 | Aquila et al. |
| 2009/0292129 A1 | 11/2009 | Napolitano et al. |
| 2010/0105917 A1 | 4/2010 | Mori et al. |
| 2010/0331546 A1 | 12/2010 | Watanabe et al. |

FOREIGN PATENT DOCUMENTS

| | | | |
|---|---|---|---|
| DE | 1064950 B | 9/1959 | |
| EP | 2123769 A1 | 11/2009 | |
| JP | 09-124595 | * 5/1997 | ........... C07D 207/14 |
| JP | 2011012032 A | 1/2011 | |
| JP | 2011236157 A | 11/2011 | |
| WO | 2007075630 A1 | 7/2007 | |
| WO | 2007112368 A1 | 10/2007 | |
| WO | 2008102720 A1 | 8/2008 | |
| WO | 2011160037 A2 | 12/2011 | |

OTHER PUBLICATIONS

Sakurai et al., Tetrahedron: Asymmetry 23 (2012) 221-224.*
English language machine translation of JP H09-124595, obtained from worldwide.espacenet.com, Accessed Feb. 27, 2021.*
Gobec, S , et al., "Methods of Molecular Transformation", Science of Synthesis, vol. 16, 195, 6 pages (2004).
Gould, R , et al., "Molecular recognition in model crystal complexes: The resolution of D and L amino acids", J Am Chem Soc 106, 7840-7842 (1984).
Hemavathi, S , et al., "Synthesis and biological screening of some new 2, 5-disubstituted 1, 3, 4-oxadiazoles", International Journal of Pharmacy and Pharmaceutical Sciences 3(4), ISSN-0975-1491, 110-114 (2011).
Jean , et al., "A convenient route to 1-benzyl 3-aminopyrrolidine and 3-aminopiperidine", Tetrahedron Letters 42, 5646-5649 (2001).
Martin, M , et al., "Efficient Recognition of Chiral Carbamoyl-α-Hydroxyacids with a Cleft-Type Receptor", Angew Chem Int Ed Engl 35(20), 2386-2388 (1996).
Nesterova, E , et al., "Substituted Ureas Based on 2,6-Dimethyl-3,5-Pyridinedicarboxylic Acid Azides", Chemistry of Heterocyclic Compounds 48(8), 1187-1195 (2012).
Nicolaides, E , "Intramolecular Curtius reaction of some hydroxy amino acids", J Org Chem 32(4), 1251-1253 (1967).
Oliva, A , et al., "Chromogenic Charge Transfer Cleft-Type Tetrahydrobenzoxanthene Enantioselective Receptors for Dinitrobenzoylamino Acids", J Org Chem 69, 6883-6885 (2004).
Patent Cooperation Treaty, International Searching Authority, Search Report and Written Opinion for PCT/EP2014/053176, 14 pages, dated Jul. 22, 2014.

(Continued)

*Primary Examiner* — Alicia L Otton
(74) *Attorney, Agent, or Firm* — Viksnins Harris Padys Malen LLP

(57) ABSTRACT

The present invention relates to a process for the preparation of enantiomerically enriched 3-aminopiperidine, as in particular of its R-enantiomer (R)-3-aminopiperidine. The invention also relates to an enantiomerically enriched intermediate of said process and to specific acid-addition salts of 3-aminopiperidine (hereinafter also APIP) that are useful for obtaining a single enantiomer of APIP, and to crystalline (R)-3-aminopiperidine-dihydrochloride-monohydrate and crystalline (S)-3-aminopiperidine-dihydrochloride-monohydrate.

17 Claims, 2 Drawing Sheets

(56) References Cited

OTHER PUBLICATIONS

Sakai, K , et al., "Chiral discrimination controlled by the solvent dielectric constant", Tetrahedron Asymmetry 15, 1073-1076 (2004).
Sakurai, et al., "Dielectrically controlled resolution (DCR) of 3-aminopiperidine via diastereomeric salt formation with N-tosyl-(S)-phenylalanine", Tetrahedron: Asymmetry 23, 221-224 (2012).
Yang, Y , "Side Reactions in Peptide Synthesis", Elsevier Science Publishing Co. Inc., Chapter 5, 111-112 (2015).

* cited by examiner

PROCESS FOR THE PREPARATION OF ENANTIOMERICALLY ENRICHED 3-AMINOPIPERIDINE

This application is a divisional of U.S. application Ser. No. 14/768,751 that was filed on Aug. 18, 2015, which is a 35 U.S.C. 371 national stage application of International Patent Application No. PCT/EP2014/053176 that was filed on Feb. 19, 2014. The entire contents of the applications referenced above are hereby incorporated by reference herein. This application also claims priority to European Patent Application No. 13156030.2 that was filed Feb. 20, 2013.

The present invention relates to a process for the preparation of enantiomerically enriched 3-aminopiperidine, and in particular of its R-enantiomer (R)-3-aminopiperidine. The invention also relates to an enantiomerically enriched intermediate of said process and to specific acid-addition salts of 3-aminopiperidine (hereinafter also APIP) that are useful for obtaining a single enantiomer of APIP, and to crystalline (R)-3-aminopiperidine-dihydrochloride-monohydrate and crystalline (S)-3-aminopiperidine-dihydrochloride-monohydrate.

BACKGROUND OF THE INVENTION

Both (R)- and (S)-3-aminopiperidine are valuable building blocks for the preparation of bioactive compounds, such as antagonistic ligands of receptors in the central nervous system. (R)-3-aminopiperidine is also known to be a key intermediate for the synthesis of dipeptidyl peptidase-4 inhibitors, such as alogliptin and linagliptin, and a protein kinase inhibitor.

Several approaches for the enantioselective preparation of (R)-3-aminopiperidine have been described in the art that rely on the cyclization of □-amino acids or their derivatives, such as D-ornithine and derivatized D-glutamic acid, or on the hydrogenation of usually derivatized 3-aminopyridine followed by enantiomeric separation. These approaches typically require expensive starting materials, a large number of synthesis steps, or expensive hydrogenation catalysts including platinum group metals, and are therefore not suitable for industrial scale syntheses.

Alternatively, 3-aminopiperidine derivatives have been prepared in the prior art, either in the form of the R-enantiomer or in the form of the racemate, via a Curtius or Hofmann rearrangement of N-protected nipecotic acid (piperidine-3-carboxylic acid) derivatives. Particular examples of this approach are the following:

US 2001/0056090 describes the synthesis of (R)-3-benzyloxycarbonylamino-1-tert-butyloxycarbonyl-piperidine by reacting N-tert-butyloxycarbonyl-protected (R)-nipecotic acid with isobutylchoroformate/triethylamine and then sodium azide. The obtained acyl azide is then subjected to a Curtius rearrangement yielding the corresponding isocyanate which is heated with benzyl alcohol to give the title compound.

Jean et al., Tetrahedron Letters 2001, 42, 5645-5649, disclose Curtius rearrangement of N-benzyl protected nipecotic acid hydrazide in the presence of sodium nitrite yielding 1-benzyl-3-aminopiperidine.

US 2010/0105917 discloses Hofmann rearrangement of (R)-nipecotic acid amide, which is N-protected with a tert-butyloxycarbonyl group or an optionally substituted benzoyl group, to the correspondingly N-protected (R)-3-aminopiperidine.

The additional steps for introducing and removing an N-protecting group that are required in the aforementioned 3-aminopiperidine synthetic routes are particularly disadvantageous for the preparation of (R)-3-aminopiperidine on an industrial scale.

Furthermore, JP 2011/012032 discloses methods for the enantiomeric resolution of racemic or insufficiently enantiomerically enriched 3-aminopiperidine, which methods are based on the crystallization of the diastereomeric acid addition salts of one of the enantiomers. According to this document (R)-3-aminopiperidine can be obtained from the racemate by crystallizing it as its acid addition salt that is formed in the presence of 2 equivalents of (R)-2-methoxy-2-phenylacetic acid or 2 equivalents of N-(para-toluene-sulfonyl)-L-phenylalanine. Unfortunately, both options are unsatisfactory as (R)-2-methoxy-2-phenylacetic acid is extremely expensive and, regarding the latter case, virtually no resolution could be obtained with N-(para-toluenesulfonyl)-L-phenylalanine, in the hands of the inventors of the present invention. Likewise, the use of N-(para-toluenesulfonyl)-L-phenylalanine in the dielectrically controlled resolution of 3-aminopiperidine via the diastereomeric acid addition salt, as described by Sakurai et al., Tetrahedron Asymmetry 2012 23, 221-224, resulted in either poor yield or insufficient enantiomeric excess.

WO 2007/075630 discloses the chiral resolution of 3-aminopiperidine via diastereomeric acid addition salts formed with dibenzoyl-L-tartaric acid, di(ortho-tolyl)-L-tartaric acid and N-acetyl-phenylalanine. However, all these chiral acids are instable and lead to only modest resolution at the most.

Therefore, there is still a strong need for providing a process for preparing APIP, that overcomes the disadvantages of the prior art. In addition, in case such a process, or another process for preparing APIP, yields racemic or insufficiently enantiomerically enriched APIP, there is also a need for a process enabling enantiomeric enrichment of APIP, in particular of (R)-APIP, which does not suffer the deficiencies of the prior art.

SUMMARY OF THE INVENTION

Surprisingly, it has been found that the first object is solved by a process for preparing 3-aminopiperidine that does not require intermediate protection of the secondary amine group of the piperidine moiety.

Therefore, according to a first aspect the present invention relates to a process for preparing 3-aminopiperidine which comprises the following steps:
a) providing piperidine-3-carboxylic acid hydrazide, and
b) transforming piperidine-3-carboxylic acid hydrazide into the piperidine-3-carbonyl azide and
c) reacting piperidine-3-carbonyl azide in the presence of water and an acid.

The reaction in step c) is a Curtius rearrangement which in general involves elimination of nitrogen gas from an acyl azide and rearrangement to the corresponding isocyanate. Hydrolysis and decarboxylation of the isocyanate then yields the corresponding amine. Thus, step c) affords the intended 3-aminopiperidine.

The Curtius rearrangement typically proceeds with retention of the configuration at the carbon atom that is attached to the carbonyl group. Accordingly the configuration at the chiral center of the piperidine-3-carboxylic acid hydrazide that is provided in step a) of the inventive process is identical with the one of the 3-aminopiperidine obtained in step c) of the process. As a consequence, the process of the invention results in a racemic, a (R)-configured or a (S)-configured 3-aminopiperidine in case a racemic, a (R)-configured or a (S)-configured piperidine-3-carboxylic acid hydrazide, respectively, is introduced into step b) of the process.

The aforementioned process of the invention is associated with several advantages. In particular, it allows the preparation of 3-aminopiperidine in a short and high yielding synthetic route that can easily be performed on an industrial scale.

It has also surprisingly been found that the second object is solved by fractional crystallization of acid addition salts of APIP with a N-modified alanine derivative, in particular the chiral carboxylic acid A which is a L-alanine or D-alanine derivative of the formula A:

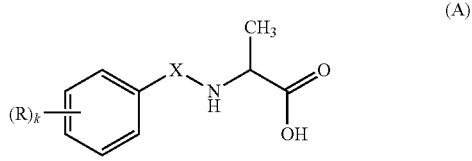

wherein X is $S(O)_2$, $C(O)$ or $NHC(O)$, k is 0, 1, 2, 3, 4 or 5 and R is CN, $NO_2$, $C_1$-$C_2$-alkyl, $C_1$-$C_2$-alkoxy or halogen, or two adjacent variables R may together represent an optionally substituted butadien-1,4-diyl radical. According to a preferred embodiment X is $S(O)_2$ or $NHC(O)$, k is 0, 1, 2 or 3 and R is $C_1$-$C_2$-alkyl, $C_1$-$C_2$-alkoxy or halogen.

Therefore, according to a second aspect the present invention relates to a process for the enantiomeric enrichment of APIP, the process comprising the fractional crystallization of APIP in the form of its acid addition salt with a chiral carboxylic acid A as described herein, where the chiral carboxylic acid is enantiomerically enriched with regard to one of its enantiomers, from a solution, emulsion or suspension containing a mixture of the enantiomers of APIP and the chiral carboxylic acid A, whereby the acid addition salt of APIP with the chiral carboxylic acid A is obtained, which is enantiomerically enriched with regard to the desired enantiomer of APIP.

The invention also relates to the novel acid addition salts of APIP with said chiral carboxylic acid A, in particular to enantiomerically enriched or enantiomerically pure acid addition salts of APIP with the carboxylic acid of the formula A. A particular embodiment of the invention relates to the acid addition salts of APIP with N-(para-toluenesulfonyl)-L-alanine, N-(para-chlorophenylsulfonyl)-L-alanine, N-(phenyl sulfonyl)-L-alanine, N-(phenylcarbamoyl)-D-alanine or N-(4-chlorophenylcarbamoyl)-D-alanine, in particular those that are enriched with regard to the R-enantiomer of APIP. Another particular embodiment of the invention relates to the acid addition salt of APIP with N-(para-toluenesulfonyl)-D-alanine, N-(para-chlorophenylsulfonyl)-D-alanine, N-(phenyl sulfonyl)-D-alanine, N-(phenylcarbamoyl)-L-alanine or N-(4-chlorophenylcarbamoyl)-L-alanine, in particular those that are enriched with regard to the S-enantiomer of APIP.

In this context, enantiomeric enrichment means that the enantiomeric excess (ee) with regard to one enantiomer of APIP in the acid addition salt is at least 50%, frequently at least 60%, in particular at least 70% or at least 80%. Particular embodiments relate to enantiomerically enriched acid addition salts of APIP with the carboxylic acid of the formula A, wherein the enantiomeric excess (ee) with regard to one enantiomer of APIP in the acid addition salt is 70% or higher, in particular 80% or higher or even 90% ee or higher such as >95 ee or >98% ee.

The use of the acid addition salt of APIP with the carboxylic acid A provides good crystallization yields and satisfactory enantiomeric enrichment generally exceeding 80:20 (ee=60%), frequently at least 85:15 (ee=70%), in particular at least 90:10 (ee=80%) or at least 95:5 (ee=90%), without using expensive chiral auxiliaries. Satisfactory enrichment can be obtained without prior enrichment of the APIP to be resolved. The crystallization of the acid-addition salt of APIP according to the invention can also be carried out in an aqueous solution, suspension or emulsion, which renders the process more economical, environment-friendly and less risky, since the use of expensive or hazardous organic solvents can be reduced or avoided.

The invention also relates to crystalline (R)-3-aminopiperidine-dihydrochloride-monohydrate, which is obtainable by using either one or both of the two aforementioned inventive processes. The enantiomeric enrichment of the R-enantiomer is preferably at least 85:15 (ee=70%), in particular at least 90:10 (ee=80%) or at least 95:5 (ee=90%).

The invention also relates to crystalline (S)-3-aminopiperidine-dihydrochloride-monohydrate, which is obtainable by using either one or both of the two aforementioned inventive processes. The enantiomeric enrichment of the S-enantiomer is preferably at least 85:15 (ee=70%), in particular at least 90:10 (ee=80%) or at least 95:5 (ee=90%).

In a further aspect, the invention relates to non-racemic piperidine-3-carboxylic acid hydrazide, which is enantiomerically enriched either with regard to its R-enantiomer or with regard to its S-enantiomer, and the acid addition salts and hydrates thereof. The enantiomeric enrichment is preferably at least 85:15 (ee=70%), in particular at least 90:10 (ee=80%) or at least 95:5 (ee=90%).

In a further aspect, the invention relates to piperidine-3-carbonyl azide, in particular to non-racemic piperidine-3-carbonyl azide, which is enantiomerically enriched either with regard to its R-enantiomer or with regard to its S-enantiomer. The enantiomeric enrichment is preferably at least 85:15 (ee=70%), in particular at least 90:10 (ee=80%) or at least 95:5 (ee=90%).

DETAILED DESCRIPTION OF THE INVENTION

In the context of the present invention, the terms used generically are defined as follows:

The term "halogen" as used herein includes e.g. fluorine, chlorine, bromine or iodine, with particular preference given to chlorine.

The term "$C_1$-$C_8$-alkyl" as used herein includes linear or branched alkyl groups having from 1 to 8, in particular 1 or 4 carbon atoms (=$C_1$-$C_4$-alkyl), such as methyl, ethyl, n-propyl, isopropyl, n-butyl, isobutyl, 1,1-dimethylethyl (=tert.-butyl), n-pentyl, n-hexyl and n-octyl.

The term "$C_1$-$C_4$-alkoxy" as used herein includes linear or branched alkoxy radicals preferably from 1 to 4, in particular 1 or 2 carbon atoms (=$C_1$-$C_2$-alkoxy), such as methoxy, ethoxy, n-propoxy, isopropoxy, n-butoxy, isobutoxy and 1,1-dimethylethyloxy.

The term "phenyl-$C_1$-$C_4$-alkyl" as used herein includes linear or branched alkyl groups having 1 to 4, in particular 1 or 2 carbon atoms, wherein one hydrogen atom is replaced by a phenyl group, such as benzyl.

The process of the invention for preparing 3-aminopiperidine, herein also called process A, comprises the following steps:

a) providing piperidine-3-carboxylic acid hydrazide, e.g. by reacting a derivative of piperidine-3-carboxylic acid (nipecotic acid), such as nipecotic acid halide or an alkyl ester or benzyl ester of nipecotic acid, with hydrazine, and b) transforming piperidine-3-carboxylic acid hydrazide into the piperidine-3-carbonyl azide, e.g. by reacting the hydrazide with an inorganic or organic nitrite compound, and c) reacting piperidine-3-carbonyl azide in the presence of water and an acid, which typically yields 3-aminopiperidine via Curtius rearrangement and subsequent hydrolysis.

Process A is suitable for providing APIP that is a racemic mixture of both enantiomers or is enriched in respect to the R- or the S-enantiomer. Process A is especially useful for generating enantiomerically enriched APIP, such as in particular APIP that is enriched with regard to the R-enantiomer or the S-enantiomer. Preferably, in order to obtain APIP in enantiomerically enriched form, either an enantiomerically enriched derivative of nipecotic acid, such as the $C_1$-$C_4$-alkyl ester or benzyl ester of (R)-nipecotic acid or the $C_1$-$C_4$-alkyl ester or benzyl ester of (S)-nipecotic acid, in particular the $C_1$-$C_4$-alkyl ester, especially the ethyl ester of (R)- or (S)-nipecotic acid, is converted in step a) into piperidine-3-carboxylic acid hydrazide or, in the alternative, the 3-aminopiperidine obtained in step c) of the process A is subjected to an enantiomeric enrichment process.

The reactions of the invention as described hereinafter are performed in reaction vessels customary for such reactions, the reaction being carried out in a continuous, semicontinuous or batchwise manner. In general, the particular reactions will be carried out under atmospheric pressure. The reactions may, however, also be carried out under reduced or elevated pressure.

The provision of piperidine-3-carboxylic acid hydrazide in step a) of process A of the invention may be accomplished by any method known in the art for preparing carboxylic acid hydrazides. Preferably, however, said provision is effected by reacting either a piperidine-3-carboxylic acid halide, such as the acid bromide or acid chloride and in particular the acid chloride, or a $C_1$-$C_4$-alkyl ester or benzyl ester of piperidine-3-carboxylic acid with hydrazine.

In process A according to the invention, hydrazine is understood to mean the hydrazine reactant, either as the anhydrous liquid, as hydrazine hydrate comprising about one molecule water per one molecule hydrazine ($N_2H_4 \cdot H_2O$) or as a solution, in particular an aqueous solution, preferably having a water content of 35 to 70% (w/w). In addition, hydrazine can also be understood to mean the hydrazine reactant as a salt of hydrazine, such as for example hydrazine acetate, hydrazine monohydrochloride, hydrazine dihydrochloride, hydrazine hemisulfate, hydrazine sulphate. Preference is given to using the hydrazine hydrate.

According to a preferred embodiment step a) of process A is accomplished by the reaction of a $C_1$-$C_4$-alkyl ester or benzyl ester (herein also called AEPC), in particular a $C_1$-$C_4$-alkyl ester of piperidine-3-carboxylic acid, especially the ethyl ester of piperidine-3-carboxylic acid, with hydrazine, preferably in the form of its hydrate. AEPC may be employed in the form of a racemic mixture or in the form of a non-racemic mixture, such as in particular a mixture that is enantiomerically enriched with regard to the R-enantiomer of AEPC or a mixture that is enantiomerically enriched with regard to the S-enantiomer of AEPC.

The reaction may be carried out with or without an explicit solvent. Suitable solvent here are water, polar organic solvents that are inert under the given reaction conditions, or a mixture of such a polar organic solvent with water. Appropriate polar organic solvents in this context are for instance $C_1$-$C_4$-alkanols, e.g. methanol, ethanol, n-propanol, isopropanol and butanol, ethers, e.g. aliphatic $C_4$-$C_{10}$-ethers having 1, 2, 3, or 4 oxygen atoms and alicyclic $C_4$-$C_6$-ethers, such as ethylene glycol dimethyl ether, diethylene glycol dimethyl ether, triethylene glycol dimethyl ether, diethyl ether, tetrahydrofuran and 1,4-dioxane, and mixtures thereof. The reaction may also be carried out in a biphasic solvent mixture comprising an aqueous phase and an aromatic solvent such as for example toluene or xylene. Preferably, however, the reaction is carried out in the absence of any explicit solvent or in a biphasic solvent mixture comprising toluene or xylene.

The aforementioned reaction of an alkyl or benzyl ester of piperidine-3-carboxylic acid with hydrazine is typically performed at a temperature in the range from 20 to 150° C., preferably in the range from 30 to 110° C., in particular in the range from 40 to 90° C. and specifically in the range from 50 to 80° C.

In relation to the alkyl or benzyl ester of piperidine-3-carboxylic acid the hydrazine is preferably used at least in equimolar amounts and more preferably in amounts of 1 to 2.0 moles per 1 mol of the ester. In case the reaction is carried out in the absence of any explicit solvent, the hydrazine is used in particular in amounts of 1 to 1.2 moles per 1 mol of the ester and specifically in amounts of 1.05 to 1.15 moles per 1 mol of the ester. In case the reaction is carried out in a biphasic solvent mixture, the hydrazine is used in particular in amounts of 1.3 to 1.8 moles per 1 mol of the ester and specifically in amounts of 1.4 to 1.6 moles per 1 mol of the ester.

According to a preferred embodiment of the invention piperidine-3-carboxylic acid hydrazide is prepared by reacting a solution of ethyl ester of piperidine-3-carboxylic acid in toluene or xylene with 1.4 to 1.6 molar equivalents of hydrazine hydrate at a temperature of 50 to 80° C.

The reaction mixture obtained in step a) of process A may be subjected to a work-up procedure or may be introduced directly into a following synthesis step either without any prior work-up or after removal of organic solvent, if present, and of a remaining excess of hydrazine that may be included in the mixture.

The work-up of the reaction mixture obtained in step a) of process A and the isolation of piperidine-3-carboxylic acid hydrazide can be effected in a customary manner. Preferably the reaction mixture is initially diluted with water or an aqueous solution of a polar organic solvent, and in particular with water. The piperidine-3-carboxylic acid hydrazide can then be crystallized from the dilution in the form of its addition salt by adding an acid that is preferably selected from mineral acids such as sulphuric acid, hydrochloric acid or hydrobromic acid, like in particular concentrated hydrochloric acid. The acid is preferably added slowly to the dilution after it has been cooled down usually to a temperature in the range of 0 to 50° C., preferably of 10 to 30° C. and in particular of 15 to 25° C., e.g. to ambient temperature. The concentrated hydrochloric acid is usually added in amounts of about 1 molar equivalent, such as 0.9 to 1.2 and in particular 0.95 to 1.1 molar equivalents, or of about 2 molar equivalents, such as 1.8 to 2.4 and in particular 1.9 to 2.2 molar equivalents, based in each case on the amount of the alkyl ester of piperidine-3-carboxylic acid used. Depending on whether about 1 molar equivalent or about 2 molar equivalents of hydrochloric acid are added, the piperidine-3-carboxylic acid hydrazide can be isolated in its monohydrochloride form or its dihydrochloride form. After completion of the crystallization the obtained crystals of the addition salt are isolated by filtration. The isolated crystals are usually washed with cold water and optionally afterwards with a polar organic solvent such as an alkanol, e.g. isopropanol and optionally thereafter with a nonpolar organic solvent such as a hydrocarbon solvent, e.g. pentane, hexane or cyclohexane. Further amounts of the addition salt can typically be obtained from the mother liquor via evaporation of the solvent and recrystallization from water or another suitable solvent or solvent mixture. The piperidine-3-carboxylic acid hydrazide is preferably isolated in the form of its monohydrochloride addition salt, which is obtained by adding about 1 molar equivalent of hydrochloric acid to the diluted reaction mixture, as described above.

Preferably the reaction mixture obtained in step a) of process A is introduced directly into a following synthesis step either without any prior work-up measures or after removal of organic solvent, if present, and of a remaining excess of hydrazine that may be included in the mixture. According to a particularly preferred embodiment of the invention reaction mixture obtained in step a) is introduced into a following synthesis step after organic solvent, if present, and of a remaining excess of hydrazine has been removed from the mixture. An excess of hydrazine is typically removed by azeotropic distillation.

According to one embodiment of the invention piperidine-3-carboxylic acid hydrazide is provided in step a) as a racemic mixture of its enantiomers, including the acid addition salts and the hydrates thereof. Such a racemic mixture is preferably prepared by reacting a racemic AEPC, in particular racemic ethyl ester of piperidine-3-carboxylic acid, with hydrazine and in particular with hydrazine hydrate.

According to a particular embodiment of the invention piperidine-3-carboxylic acid hydrazide is provided in step a) as a non-racemic mixture of its enantiomers, where the mixture is enantiomerically enriched with regard to one of its enantiomers, in particular with regard to its R-enantiomer. Said non-racemic mixture of the enantiomers of piperidine-3-carboxylic acid hydrazide is herein also called enantiomerically enriched piperidine-3-carboxylic acid hydrazide. In this context enantiomeric enrichment means that the enantiomeric excess (ee) with regard to one enantiomer of piperidine-3-carboxylic acid hydrazide in the non-racemic mixture is at least 50%, frequently at least 60%, in particular at least 70% or at least 80%. Preferred embodiments of the invention relate to enantiomerically enriched non-racemic mixtures of piperidine-3-carboxylic acid hydrazide, wherein the enantiomeric excess (ee) with regard to one enantiomer of piperidine-3-carboxylic acid hydrazide in the acid addition salt is 90% ee or higher such as >95% ee or >98% ee.

A particular embodiment of the invention relates to piperidine-3-carboxylic acid hydrazide, which is enantiomerically enriched with regard to one of its enantiomers, in particular with regard to its R-enantiomer or to an acid addition salt thereof, such as a sulphate, hydrogensulfate, hydrochloride or hydrobromide, or a hydrate thereof.

Said enantiomerically enriched piperidine-3-carboxylic acid hydrazide is preferably prepared in step a) by reacting AEPC, in particular ethyl ester of piperidine-3-carboxylic acid, which is enantiomerically enriched with regard to one of its enantiomers, in particular its R-enantiomer, with hydrazine and in particular with hydrazine hydrate.

Enantiomerically enriched AEPC, in turn, can be obtained by any method known in the art for this or a similar purpose, for example by asymmetric synthesis, by synthesis starting from a chiral precursor, such as enantiomerically enriched piperidine-3-carboxylic acid, or by enantiomeric enrichment of a mixture of the AEPC enantiomers.

Enantiomeric enrichment of AEPC can be accomplished by customary methods, e.g. by chiral chromatography or by separation of the diastereomers that can be generated by derivatizing AEPC with a chiral resolving agent. Preferred chiral resolving agents in this context are chiral acids capable of forming diastereomeric acid addition salts that can be enriched regarding one enantiomer of the $C_1$-$C_4$-alkylester or benzyl ester of piperidine-3-carboxylic acid, for example by fractional crystallization.

According to a preferred embodiment of the invention step a) of process A comprises subjecting racemic AEPC, in particular the racemic ethyl ester of piperidine-3-carboxylic acid, to enantiomeric enrichment by fractional crystallization of an acid addition salt of AEPC with a chiral acid. However, it is also possible to enrich non-racemic mixtures of the AEPC enantiomers in this manner. This enantiomeric enrichment can be used to enrich the R-enantiomer or the S-enantiomer of the AEPC, and is preferably used to enrich the R-enantiomer. Preferred chiral acids in this respect or those known in the art, such as tartaric acid, as described for example in U.S. Pat. No. 5,220,016 and in WO 00/56730, or mandelic acid or dibenzoyl tartaric acid as described in EP1341762, or ethers of 2-hydroxy-propionic acid as described in U.S. Pat. No. 6,340,762. Enantiomeric enrichment of the R-enantiomer of AEPC is preferably achieved by crystallization of the acid addition salt of AEPC with one of the following acids: L(+) tartaric acid or D-mandelic acid. Enantiomeric enrichment of the S-enantiomer of AEPC is preferably achieved by crystallization of the acid addition salt of AEPC with one of the following acids: D(−) tartaric acid or L-mandelic acid.

As outlined above, the fractional crystallization of AEPC with a chiral acid results in crystals of acid addition salts of AEPC which are enantiomerically enriched with regard to (R)- or (S)-AEPC. Thus, the mother liquor obtained in said crystallizations is depleted with regard to this respective enantiomer of AEPC and therefore contains an excess of the opposite enantiomer of AEPC. For example, the mother liquor obtained from the crystallization of (R)-AEPC acid addition salts is enriched with regard to (S)-AEPC. In order to avoid loss of yield the APEC of said mother liquor may be subjected to a racemization. In this way, subsequent to the racemization, an additional amount of the desired enantiomer of APEC, such as (R)-AEPC, can be prepared by means of enantiomeric enrichment, for example according to the methods involving fractional crystallization mentioned above. Racemization of non-racemic AEPC is usually accomplished by treating AEPC with a base according to known procedures that are described for example in WO02/068391. Suitable methods include e.g. treatment with catalytic amounts of sodium ethoxylate as base.

The acid addition salts of AEPC with a chiral acid obtained by the methods for enantiomeric enrichment of the preceding embodiment can be transformed into the free base, i.e. free AEPC, according to well-known techniques. Typically, for preparing the free base the acid addition salt of AEPC is treated either with a diluted aqueous base, such as an aqueous solution of an alkali metal carbonate, alkali metal hydrogen carbonate or alkali metal hydroxide such as sodium carbonate, potassium carbonate, sodium hydrogen carbonate, sodium hydroxide, calcium hydroxide or potassium hydroxide, or with a basic ion exchange resin. The free base may be extracted from the thus obtained mixture by a suitable method, such as extraction with an organic solvent. The addition of base is preferably conducted under cooling. It is further preferred to use a concentrated aqueous solution of a base.

In step b) of the process A the piperidine-3-carboxylic acid hydrazide obtained in step a) is converted into piperidine-3-carbonyl azide. The reaction is usually carried out by contacting the piperidine-3-carboxylic acid hydrazide with a nitrite under acidic conditions in a solvent using suitable reaction conditions. The piperidine-3-carboxylic acid hydrazide may be used as its free base or as an acid addition salt thereof or a hydrate thereof, in particular as the free base or as the acid addition salt thereof with a mineral acid such as hydrochloric acid, sulphuric acid or hydrobromic acid.

Piperidine-3-carboxylic acid hydrazide is typically employed in step b) as is, i.e. as the free base, or as its acid addition salt, in particular as its monohydrochloride or as its dihydrochloride, and is preferably employed as the free base.

In process A according to the invention, nitrite is understood to mean both inorganic and organic nitrites, including nitrous acid, one of its salts, and organic nitrite or a mixture thereof. Suitable salts of nitrous acid are in particular its alkali metal salts, e.g. sodium nitrite, potassium nitrite or lithium nitrite, and its alkali earth metal salts, such as calcium nitrite or barium nitrite. Preferred salts here are alkali metal salts, in particular sodium nitrite and potassium nitrite. The term "organic nitrite" in this context means a straight-chain or branched $C_1$-$C_8$-alkyl nitrite, such as methyl nitrite, ethyl nitrite, n-propyl nitrite, isopropyl nitrite, n-butyl nitrite, isobutyl nitrite, tert-butyl nitrite, n-pentyl nitrite, isopentyl nitrite (isoamyl nitrite), neopentyl nitrite (2,2-dimethylpropyl nitrite), n-hexyl nitrite and 2-ethylhexyl nitrite, a $C_5$-$C_8$-cycloalkyl nitrite, such as cyclohexyl nitrite, a phenyl-$C_1$-$C_4$-alkyl nitrite, such as benzyl nitrite, or a mixture thereof. Preferred organic nitrites for use in process A are n-butyl nitrite, isobutyl nitrite, tert-butyl nitrite, n-pentyl nitrite, isopentyl nitrite and mixtures thereof, and particular preference is given to tert-butyl nitrite, isopentyl nitrite and a mixture thereof.

According to a special embodiment of the invention the nitrite used in process A is isopentyl nitrite, butyl nitrite or sodium nitrite and in particular isopentyl nitrite or butyl nitrite.

The nitrite is used in the conversion of step b) in an amount of usually 1 to 2 molar equivalents, preferably 1 to 1.5 molar equivalents and in particular 1.05 to 1.4 molar equivalents, based on the amount of piperidine-3-carboxylic acid hydrazide used.

Typically the conversion of step b) is carried out in the presence of 1 to 4 molar equivalents, preferably 1.2 to 3 molar equivalents, more preferably 1.5 to 2.5 molar equivalents and in particular 1.7 to 2.3 molar equivalents of an acid, based on the amount of piperidine-3-carboxylic acid hydrazide used.

The amount of acid to be added to the reaction mixture depends on the forms in which the nitrite and the piperidine-3-carboxylic acid hydrazide are employed in the conversion of step b). For instance, if nitrite is employed as nitrous acid it is generally advisable to reduce the amount of acid to be added by the corresponding number of molar equivalents. Likewise, if piperidine-3-carboxylic acid hydrazide is employed as its acid addition salt, e.g. as its mono- or dihydrochloride, the amount of acid to be added should be correspondingly reduced. Thus, if the dihydrochloride of piperidine-3-carboxylic acid hydrazide is used in step b) additional acid is usually not required.

Suitable acids are in particular strong acids, such as hydrochloric acid, sulphuric acid or organic sulfonic acids, such as alkylsufonic acids or arylsulfonic acids. Preference is given here to hydrochloric acid.

Solvents that are suitable for the reaction in step b) include water and polar organic solvents and mixtures thereof. Examples of suitable polar organic solvents are in particular alcohols, such as $C_1$-$C_5$-alkanols, e.g. methanol, ethanol, n-propanol, isopropanol, n-butanol, isobutanol, tert.-butanol or n-pentanol, $C_1$-$C_4$-carboxylic acids, such as acetic acid or propionic acid, 5- and 6-membered lactones such as □-butyrolactone, polyols and polyetherols, such as ethylene glycol, propylene glycol, glycerol, dimethoxyethane, ethylendiglycol or ethylenglycolmonomethylether.

Preferred polar organic solvents here are $C_1$-$C_4$-alkanols, in particular isopropanol, and $C_1$-$C_3$-carboxylic acids, in particular acetic acid. Preferred solvents for use in step b) of the inventive process A are water and mixtures of water with $C_1$-$C_4$-alkanols, such as isopropanol, or with $C_1$-$C_3$-carboxylic acids, such as acetic acid. Particular preference is given to water.

The total amount of solvent used in step b) of the process A according to the invention is usually in the range from 100 to 1000 g, preferably in the range from 250 to 800 g and in particular in the range from 350 to 700 g, based on 1 mol of piperidine-3-carboxylic acid hydrazide.

The piperidine-3-carboxylic acid hydrazide and the nitrite can in principle be contacted with one another in any desired sequence. For example, the piperidine-3-carboxylic acid hydrazide, if appropriate dissolved in a solvent or in dispersed form, can be initially charged and admixed with the nitrite or, conversely, the nitrite, if appropriate dissolved in a solvent or in dispersed form, can be initially charged and admixed with the piperidine-3-carboxylic acid hydrazide. Alternatively, these two components can also be added simultaneously to the reaction vessel. If required, an acid can be added to the vessel before or after the addition of the piperidine-3-carboxylic acid hydrazide or else together with it.

It has been found to be appropriate to initially charge the reaction vessel with piperidine-3-carboxylic acid hydrazide (in the form of its free base or in the form of an acid addition salt thereof or a hydrate thereof), preferably dissolved or dispersed in at least part of the solvent, and then add the acid, if required, while keeping the reaction mixture at a temperature of about −10 to 10° C. and preferably of about −5 to 5°. Afterwards the nitrite is typically added either continuously or stepwise at a temperature of about −25 to 5° C. and preferably of about −18 to 0° C., depending on the reaction conditions of the individual case. After the addition of the nitrite is completed the reaction mixture is allowed to warm up to temperature of −5 to 5° C., preferably −3 to 3° C., and agitated for about 10 minutes to 4 hours and preferably for about 20 minutes to 2 hours.

The work-up of the reaction mixture obtained from the conversion in step b) and the isolation of the piperidine-3-carbonyl azide can, if desired, be effected in a customary manner, for example by removing the solvent, e.g. under reduced pressure, or by precipitation. Preferably, however, the reaction product obtained from the conversion in step b) is subjected, without preceding work-up, to the conversion in step c) of the process A according to the invention. To this end, the reaction mixture obtained after the completion of the conversion in step b) is typically introduced directly to the conversion in step c).

Thus, according to a particular preferred embodiment of the invention steps b) and c) of process A are performed without intermediate isolation of piperidine-3-carbonyl azide.

In step c) of the process A the piperidine-3-carbonyl azide obtained in step b) is converted into 3-aminopiperidine (APIP). The reaction is usually carried out by heating piperidine-3-carbonyl azide in a solvent I under hydrolytic conditions.

It has generally been found to be advantageous to initially provide a solution or dispersion of piperidine-3-carbonyl azide in a solvent I that is selected from the solvents mentioned above as suitable for the conversion in step b) and in particular from those mentioned there as preferred. Piperidine-3-carbonyl azide is usually solved or dispersed in 100 to 1000 g, preferably in 250 to 800 g and in particular in 350 to 700 g of the solvent I, based on 1 mol of piperidine-3-carbonyl azide.

According to a preferred embodiment of the invention said solution or dispersion of piperidine-3-carbonyl azide is provided in the form of the reaction mixture obtained after the conversion in step b) of the process A, i.e. after completion of the reaction in step b) the reaction mixture is used as said initial solution or dispersion of piperidine-3-carbonyl azide in step c).

Typically, the initially provided solution or dispersion of piperidine-3-carbonyl azide is then added either continuously, stepwise or in one portion, and preferably continuously or stepwise, to a solvent II which has a temperature in the range of 50 to 150° C., preferably in the range of 70 to 120° C. and in particular in the range of 75 to 100° C. Thereafter the reaction mixture is kept at about this temperature for a period of 2 minutes to 4 hours, preferably 5 minutes to 2 hours and in particular 8 minutes to 1.5 hours, and afterwards cooled to about ambient temperature.

Suitable solvents II are those mentioned above as suitable for the conversion in step b). Particular preference is given, however, to water as solvent II.

The work-up of the reaction mixture obtained in step c) of the process A and the isolation of APIP can be achieved by methods customary in the art, such as removal of the solvent, e.g. under reduced pressure, extraction of an aqueous solution of APIP with an non-water miscible organic solvent, precipitation, e.g. crystallization of 3-aminopiperidine as its mono- or dihydrochloride, or a combination of these measures. Alternatively, the reaction mixture obtained from the conversion in step c) may be subjected, without any preceding work-up steps, to a process for the enantiomeric enrichment of APIP, and in particular one that is based on the fractional crystallization of APIP in the form of its addition salt with a chiral acid.

Preferably, for work-up, after the addition of 0.5 to 2.5 molar equivalents, and in particular 0.8 to 2.0 molar equivalents, of hydrochloric acid, based on the amount of piperidine-3-carbonyl azide used, the reaction mixture is concentrated by removing at least a major portion of the solvent. The remaining material may optionally be taken up in water, concentrated, taken up in an appropriate organic solvent, such as in particular isopropanol and concentrated again. The resulting residue is dissolved, preferably with heating, in a relative small amount of a polar organic solvent, such as in particular methanol. To the obtained solution, after cooling it to about ambient temperature, was gradually added a less polar organic solvent, such as in particular acetone or isopropanol, in amounts about 30 to 300% by weight, relative to the amount of the aforementioned polar organic solvent. In case an enantiomerically enriched APIP has been synthesized before the addition of said less polar solvent the solution may optionally be seeded with the corresponding crystalline hydrochloride. The thus obtained precipitate is optionally dried via azeotropic distillation under reduced pressure after adding for example isopropanol or a mixture of isopropanol with methanol, and to the resulting suspension the aforementioned polar solvent, such as methanol, is added, optionally with heating, and then the aforementioned less polar solvent, such as acetone or isopropanol, is again gradually added. The product obtained after the first or the second precipitation step is one of the hydrochloride salts of APIP, such as the monohydrochloride, the dihydrochloride or the dihydrochloride monohydrate.

According to a preferred embodiment of the invention 3-aminopiperidine is isolated from step c) as its dihydrochloride or dihydrochloride monohydrate.

According to a particular preferred embodiment of the invention 3-aminopiperidine, if it is obtained as its R- or S-enantiomer in enriched form, is isolated from step c) as its dihydrochloride or as its dihydrochloride monohydrate.

In case the APIP obtained in step c) of the process A according to the invention is racemic or of insufficient enantiomeric purity it may be subjected to enantiomeric enrichment in particular by fractional crystallization of APIP in the form of its acid-addition salt with a chiral carboxylic acid of the formula A according to the second aspect of the invention.

According to the second aspect of the present invention, optical resolution of the enantiomers of 3-aminopiperidine is achieved by fractional crystallization of the respective enantiomers in the form of their diastereomeric acid addition salts with a N-modified alanine derivative of the formula A as described above.

Therefore the invention also relates to a process for the enantiomeric enrichment of APIP, which is herein also called process B. The process comprises the fractional crystallization of APIP in the form of its acid-addition salt with either a N-modified L-alanine derivative or a N-modified D-alanine derivative from a solution, emulsion or suspension containing a mixture of the enantiomers of APIP, in particular a racemic mixture, and either the N-modified L-alanine derivative or the N-modified D-alanine derivative.

Suitable N-modified L-alanine derivatives are the L-alanine derivatives of the formula A-L while suitable N-modified D-alanine derivatives are the D-alanine derivatives of the formula A-D, but are not limited thereto:

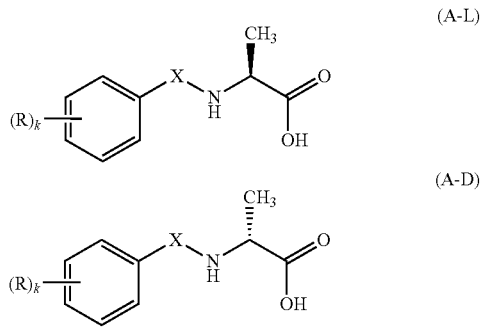

wherein k is 0, 1, 2, 3, 4 or 5, R is CN, $NO_2$, $C_1$-$C_2$-alkyl, $C_1$-$C_2$-alkoxy or halogen, or two adjacent variables R may together represent an unsubstituted or substituted butan-1,3-dien-1,4-diyl, and X is $S(O)_2$, $C(O)$ or $NHC(O)$. In case the variable X is $NHC(O)$ the nitrogen atom of the diradical NHC(O) is linked to the benzene ring. In formulae A, A-L and A-D the variables k, R and X, independently of each other, have preferably the following meanings: The variable k is preferably 0, 1, 2 or 3. X is preferably $S(O)_2$ or NHC(O). R is preferably $C_1$-$C_2$-alkyl, $C_1$-$C_2$-alkoxy or halogen.

The alanine derivatives of the formulae A-L and A-D are herein also called chiral carboxylic acids A-L and A-D, respectively (herein also named CAA).

Preferred herein are chiral carboxylic acids A-L and A-D wherein the variable X is $S(O)_2$ or NHC(O), the variable k is 0 or 1 and the variable R is $C_1$-$C_2$-alkyl, in particular methyl, or halogen, in particular $C_1$.

According to preferred embodiment of the invention the chiral carboxylic acids A-L and A-D are of the formulae A-L or A-D, respectively, wherein X is $S(O)_2$, k is 0 or 1, and R, if present, is methyl or chloride and preferably linked in the para position in relation to the variable X. These carboxylic acids A-L and A-D are herein also called carboxylic acids A-1-L and A-1-D, respectively.

Particular preferred carboxylic acids A-1-L are (S)-2-(4-methylphenyl)sulfonylamino-propionic acid (also known as N-(para-toluenesulfonyl)-L-alanine which is herein also named Ts-L-Ala), (S)-2-(4-chlorophenyl)sulfonylamino-propionic acid (also known as N-(para-chlorophenylsulfonyl)-L-alanine which is herein also named pCl-Ps-L-Ala) and (S)-2-phenylsulfonylamino-propionic acid (also known as N-(phenylsulfonyl)-L-phenylalanine which is herein also named Ps-L-Ala).

Particular preferred carboxylic acids A-1-D are (R)-2-(4-methylphenyl)sulfonylamino-propionic acid (also known as N-(para-toluenesulfonyl)-D-alanine which is herein also named Ts-D-Ala), (R)-2-(4-chlorophenyl)sulfonylamino-propionic acid (also known as N-(para-chlorophenylsulfonyl)-D-alanine which is herein also named pCl-Ps-D-Ala) and (R)-2-phenylsulfonylamino-propionic acid (also known as N-(phenylsulfonyl)-D-phenylalanine which is herein also named Ps-D-Ala).

According to another preferred embodiment of the invention the chiral carboxylic acids A-L and A-D are of the formulae A-L or A-D, wherein X is NHC(O), k is 0 or 1, and R, if present, is halogen, in particular chlorine, and preferably linked in the para position in relation to the variable X. These carboxylic acids A-L and A-D are herein also called carboxylic acids A-2-L or A-2-D, respectively.

Particular preferred carboxylic acids A-2-L are (S)-2-(3-phenylureido)-propionic acid (also known as N-phenylcarbamoyl-L-alanine which is herein also named PC-L-Ala) and (S)-2-(3-(4-chlorophenyl)ureido)-propionic acid (also known as N-(4-chlorophenylcarbamoyl)-L-alanine which is herein also named Cl-PC-L-Ala).

Particular preferred carboxylic acids A-2-D are (R)-2-(3-phenylureido)-propionic acid (also known as N-phenylcarbamoyl-D-alanine which is herein also named PC-D-Ala) and (R)-2-(3-(4-chlorophenyl)ureido)-propionic acid (also known as N-(4-chlorophenylcarbamoyl)-D-alanine which is herein also named Cl-PC-D-Ala).

It has been found that the R-enantiomer of APIP can be selectively crystallized from a mixture of APIP enantiomers by using the carboxylic acids A-1-L as N-modified L-alanine derivative in the inventive process B, while the S-enantiomer of APIP can be selectively crystallized from a mixture of APIP enantiomers by using the carboxylic acids A-2-L.

It has also been found that the S-enantiomer of APIP can be selectively crystallized from a mixture of APIP enantiomers by using the carboxylic acids A-1-D as N-modified D-alanine derivative in the inventive process B, while the R-enantiomer of APIP can be selectively crystallized from a mixture of APIP enantiomers by using the carboxylic acids A-2-D.

Thus, in a particular aspect the present invention provides a process for obtaining the R-enantiomer of APIP, which comprises fractional crystallizing said R-enantiomer as its diastereomeric salt with a carboxylic acids A-1-L from a solution or suspension of a mixture of the enantiomers of APIP in at least one solvent.

Likewise, in another particular aspect the invention provides a process for obtaining the S-enantiomer of APIP, which comprises fractional crystallizing said S-enantiomer as its diastereomeric salt with a carboxylic acids A-2-L from a solution or suspension of a mixture of the enantiomers of APIP in at least one solvent.

In a further particular aspect the present invention provides a process for obtaining the S-enantiomer of APIP, which comprises fractional crystallizing said S-enantiomer as its diastereomeric salt with a carboxylic acids A-1-D from a solution or suspension of a mixture of the enantiomers of APIP in at least one solvent.

Yet, in a further particular aspect the invention provides a process for obtaining the R-enantiomer of APIP, which comprises fractional crystallizing said R-enantiomer as its diastereomeric salt with a carboxylic acids A-2-D from a solution or suspension of a mixture of the enantiomers of APIP in at least one solvent.

According to process B of the invention the acid addition salt of (R)- or (S)-APIP with a chiral carboxylic acid A-L or A-D (CAA) is typically crystallized from a suspension or a solution containing the mixture of APIP enantiomers suspended or dissolved, respectively, in a suitable solvent or solvent mixture.

The mixture of the APIP enantiomers contained in the suspension or in the solution may be a racemic mixture or a non-racemic mixture. If a non-racemic mixture is used, the excess of one enantiomer will generally not exceed 30%, in particular 20%, i.e. the S/R-ratio (or R/S-ratio, respectively) will be in the range from 70:30 to 30:70, in particular in the range from 60:40 to 40:60. Such non-racemic mixtures may be obtained during crystallization of one of the enantiomers from a solution of the racemic mixture of APIP or by addition of racemic APIP to a mother liquor from which one of the enantiomers had already been crystallized. Racemic mixtures as well as non-racemic mixtures can be used both in the process B according to the present invention.

The crystallization of the diastereomeric acid addition salt of APIP with a CAA, in particular with those mentioned as preferred, in the process B of the invention can be performed by analogy to standard techniques for the optical resolution of enantiomeric mixtures of compounds having a basic nitrogen atom with chiral acids, e.g. by analogy to the methods described in the prior art cited in the introductory part of the present application.

In particular, the crystallization of APIP is performed in the presence of suitable amounts of the suitable CAA. Needless to say, the amount of the CAA is chosen to ensure crystallization of the diastereomeric acid addition salt of APIP with the CAA. Usually, the amount of the CAA used is at least 0.8 mol, in particular at least 0.9 mol per mol of the desired APIP enantiomer (i.e. (S)-APIP or (R)-APIP, depending on which enantiomer shall be crystallized) which is present in the solution or slurry before crystallization. Preferably, CAA is used in an amount of 0.9 to 5 moles per mol of the desired APIP enantiomer which is contained in the solution or slurry before crystallization. Preferably, the CAA is used in an amount of 1.5 to 4.5 moles, in particular 1.8 to 4.2 moles, per mol of the desired APIP enantiomer which is contained in the solution or slurry before crystallization, when the solution or suspension contains a racemic mixture or a mixture of APIP enantiomers, wherein the relative amount of R- and S-enantiomer of APIP is close to 1:1 (i.e. from 45:55 to 55:45).

The term "suitable CAA" means the CAA which is particularly suitable for crystallizing the respective APIP enantiomer—i.e. in case of (R)-APIP the suitable CAA is a carboxylic acid A-1, in particular those mentioned herein as preferred, while in case of (S)-APIP the suitable CAA is a carboxylic acids A-2, in particular those mentioned herein as preferred.

In order to achieve a high enantiomeric enrichment of the desired APIP enantiomer, the optical purity of the suitable CAA used in the crystallization will generally be at least 70% ee, frequently at least 80% ee, preferably at least 90% ee, in particular at least 95% ee and more preferably at least 99% ee.

Preferably, the molar amount of CAA used in the process B according to the present invention does not exceed more than 2.5 times the total molar amount of APIP present in the solution or suspension before crystallization. In particular, the CAA is used in an amount from 0.5 to 2.5 moles, more preferably from 0.8 to 2.2 mol per mol of APIP which is contained in the solution or suspension before crystallization.

In case the APIP is employed in process B in the form of one of its hydrochloride addition salts, such as the monohydrochloride or the dihydrochloride of APIP, said addition salts are generally transformed into the free base prior to the crystallization according to well-known techniques. For this purpose the hydrochloride addition salts of APIP are usually treated with about 1 molar equivalents or about 2 molar equivalents of an aqueous base, depending on whether the monohydrochloride or the dihydrochloride of APIP is used. Suitable aqueous bases are aqueous solutions of ammonia, of a primary, secondary or tertiary amine, such as methylamine, diethylamine, triethylamine, ethanolamine or triethanolamine, of an alkali metal carbonate, alkali metal hydrogen carbonate or alkali metal hydroxide, such as sodium carbonate, potassium carbonate, sodium hydrogen carbonate, sodium hydroxide, calcium hydroxide or potassium hydroxide. Preference is given to alkali metal hydroxide and in particular sodium hydroxide. It is preferred to add the aqueous base in one portion or gradually to a solution of the hydrochloride addition salt of APIP in water or in one of the mixtures of water with a water-miscible organic solvent described below. The thus obtained mixture including the free base of APIP is typically directly subjected to the crystallization of process B without any preceding work-up steps. Alternatively, it is also possible to transform the hydrochloride addition salts of APIP into the free base by means of ion exchange resins.

For the crystallization according to process B of the present invention, CAA and the mixture of the APIP enantiomers is dissolved or suspended in a suitable solvent or solvent mixture. Preferably, CAA and the mixture of APIP enantiomers are completely dissolved prior to crystallization.

The solution of CAA and the APIP enantiomers can be a homogeneous solution, i. e. CAA, the mixture of enantiomers and at least one solvent form a single phase prior to crystallization, or a heterogeneous solution (multi-phase solution, such as an emulsion), wherein CAA and the mixture of enantiomers are dissolved in at least one solvent or in a mixture of at least two solvents of different polarity, thereby forming a multi-phase liquid. Both, the homogeneous solution and the emulsion may further comprise solid material, in particular undissolved APIP enantiomers or undissolved CAA. Preferably, no undissolved APIP and no undissolved CAA are present prior to crystallization.

Suitable solvents include in particular water, polar organic solvents and mixtures thereof with water. Suitable organic solvents include organic solvents which are at least partially water-miscible, i.e. which have a miscibility with water of at least 20% (v/v) at 20° C., and also solvents which have a reduced miscibility with water, i.e. which have a miscibility with water of below 20% (v/v), in particular below 10% (v/v) at 20° C., Suitable organic solvents which are at least partially water-miscible, i.e. which have a miscibility with water of at least 20% (v/v) at 20° C., include, but are not limited to:
1. $C_1$-$C_4$-alkanols, such as methanol, ethanol, n-propanol or isopropanol;
2. $C_1$-$C_4$-carboxylic acids, such as formic acid, acetic acid or propionic acid;
3. amides, N-methylamides and N,N-dimethylamides of $C_1$-$C_3$-carboxylic acids, such as formamide, dimethylformamide (DMF), acetamide and N,N-dimethylacetamide;
4. 5 or 6-membered lactames with a total of 7 carbon atoms, such as pyrrolidone, N-methylpyrrolidone, N-ethylpyrrolidone, N-isopropylpyrrolidone, N-hydroxyethylpyrrolidone;
5. Dimethylsulfoxid and sulfolane;
6. Ketones having 3 to 6 carbon atoms, such as acetone, 2-butanone, 2-pentanone, 3-pentanone, cyclopentanone and cyclohexanone;
7. acetonitrile;
8. 5- or 6-membered lactones, such as □-butyrolactone;
9. polyols and polyetherols, such as glycol, glycerin, dimethoxyethan, ethylenglycolmonomethylether, diethyleneglycoldimethylether, triethyleneglycol-dimethylether, dipropyleneglycoldimethylether etc,
10. Cyclic ethers, such as tetrahydrofurane, dioxane and trioxane,
11. low molecular weight polyethyleneglycoles and low molecular weight polypropyleneglycoles (MW≤400).

Suitable organic solvents which have a reduced miscibility with water, i.e. which have a miscibility with water of below 20% (v/v), in particular at most 10% (v/v) at 20° C., include, but are not limited to:
12. aromatic solvents, such as benzene or its derivatives like toluene, benzonitrile, nitrobenzene, chlorobenzene or xylene and heteroaromatic liquids such as pyridine or furane;
13. halogenated alkanes like dichloromethane, dichloroethane, trichloroethane;
14. dialkyl ethers having ≥4, e.g. 4 to 10 carbon atoms, such as diethylether, tert.-butyl ethylether, diisopropylether or tert-butylmethylether;
15. esters of n-, i- or branched carboxylic acids with ≥5 carbon atoms, including diesters, triesters, such as oils and fats, and polyesters;
16. alkanoles, aromatic and cyclic alcohols with ≥5, e.g. 5 to 10 carbon atoms, e.g. 2-hexanol, cyclohexanol, benzylalcohol or octanol.

According to a preferred embodiment of the crystallization in the process B according to the present invention the solution of CAA and the APIP enantiomers is a homogeneous solution.

Preferred solvents for the crystallization in process B comprise at least one protic solvent, which is selected from water, $C_1$-$C_4$-alkanols, such as methanol, ethanol or isopropanol, and $C_1$-$C_4$-carboxylic acids, such as acetic acid. These solvents may be used as such, as a mixture or in a mixture with an aprotic solvent, in particular an aprotic solvent having a reduced water solubility, e.g. an aprotic solvent having a water solubility of <20% (v/v), especially ≤10% (v/v) at 20° C.

In a very preferred embodiment of the crystallization of process B, the solvent which is used for forming the solution or suspension comprises water or at least one $C_1$-$C_4$-alkanol, such as preferably ethanol. In particular the solvent is water, a $C_1$-$C_4$-alkanol, such as in particular ethanol, a mixture of 2, 3 or 4 and in particular 2 $C_1$-$C_4$-alkanols, such as a mixture of ethanol and methanol, or a mixture of water with either a $C_1$-$C_4$-alkanol or a $C_1$-$C_4$-carboxylic acid, such as in particular a mixture of water with ethanol or with acetic acid.

In case the APIP is introduced into the crystallization according to process B in the form of its free base, the solvent used for forming the solution or suspension is preferably selected from $C_1$-$C_4$-alkanol, such as in particular ethanol, and mixtures of water with a $C_1$-$C_4$-alkanol, such as ethanol. In this context the ratio of water to $C_1$-$C_4$-alkanol in mixtures of water with a $C_1$-$C_4$-alkanol is the range from 20:80 (v/v) to 80:20 (v/v), and in particular from 40:60 (v/v) to 60:40 (v/v).

In case the APIP is introduced into the crystallization according to process B in the form of one of its hydrochloride addition salts, the solvent used for forming the solution or suspension is in preferably selected from water and mixtures of water with a $C_1$-$C_4$-carboxylic acid, such as acetic acid. In this context the mixtures of water with a $C_1$-$C_4$-carboxylic acid consist of up to 10% by weight and preferably up to 5% by weight, such as 0.5 to 10% by weight, and in particular 1.5 to 5% by weight, of the $C_1$-$C_4$-carboxylic acid.

In case an aqueous base is added to transform a hydrochloride addition salt of APIP into its free base, as described above, the solvent included in the volume of the aqueous base contributes to the aforementioned solvent used for forming a solution or suspension of CAA and APIP enantiomers in process B and therefore is also part of its total amount.

The crystallization of the diastereomeric acid addition salt of APIP with CAA from the solution or suspension containing the mixture of APIP enantiomers may be achieved by conventional crystallization techniques know in the art. Usually, CAA and the mixture of the APIP enantiomers is suspended or preferably dissolved in a suitable solvent to obtain a suspension or preferably a solution of CAA and the APIP enantiomers in said solvent.

The concentration of APIP in the suspension or solution is usually from 1 to 20% by weight, in particular from 3 to 10% by weight and more preferably from 3.5 to 5.5% by weight, based on the total amount of solvent and APIP in the form of its free base. The total amount of APIP and CAA will generally not exceed 40% by weight, in particular 25% by weight and more preferably 17% by weight, based on the total amount of APIP, CAA and solvent.

In order to sufficiently suspend or dissolve CAA and the APIP enantiomers it is usually advantageous to heat the solution or suspension to a temperature of 30° C. to 150° C., preferably 40 to 120° C. and in particular 50 to 100° C. for a suitable period of time. How such a solution of suspension of CAA and the APIP enantiomers in the solvent is accomplished in detail is usually of secondary relevance. Thus, CAA and the APIP enantiomers may be added together to the solvent which is then heated, or CAA may be added to a hot solution of the APIP enantiomers, to name only 2 of the possible options. The crystallization is typically affected by cooling the solution or suspension to temperature of generally below 65° C., such as a temperature in the range of 10 to 65° C., preferably 15 to 45° C. and in particular 18 to 42° C.

In order to assist the crystallization, it may be advantageous to dilute the solution or suspension containing APIP and CAA with a solvent that is miscible with the solvent used for preparing the solution or suspension and in addition has a lower polarity. For instance, crystallization from a solution or suspension with a $C_1$-$C_4$-alkanol, e.g. ethanol, as sole or predominant solvent can favourably be initiated by adding another $C_1$-$C_4$-alkanol having a lower polarity, e.g. isopropanol. The amount of the less polar $C_1$-$C_4$-alkanol to be added to the solution or suspension is preferably from 20 to 80% by weight, in particular 40 to 60% by weight, relative to the amount of original solvent. Another option to induce crystallization is to add seed crystals of the acid-addition salt of the desired APIP enantiomer with the suitable CAA to the solution or slurry containing APIP and CAA. The amount of seed crystals to be added to the solution or suspension is preferably from 0.1 to 10 mmol, preferably from 0.2 to 8 mmol, in particular from 0.3 to 5 mmol, per mol of the compound of APIP contained in the solution.

The thus formed acid addition salt of APIP with CAA is then separated from the mother liquor by conventional separation techniques such as filtration and centrifugation. The thus obtained crystalline material, after optionally washing it initially with the mother liquor, may be washed with a suitable solvent, e. g. with water and/or a solvent in which the acid addition salt is only sparingly soluble or even insoluble to remove mother liquor and further impurities, in particular acid addition salts of the non-desired APIP enantiomer. Preferably, after optionally washing with the mother liquor, the crystalline material is subjected to successive washes using solvents of declining polarity, e.g. after washing with water the crystals may be washed with a $C_2$-$C_6$-alkanol such as n-butanol or isobutanol, then with a di-$C_1$-$C_4$-alkyl ether such as diethyl ether, diisopropyl ether, tert-butylmethyl ether or tert-butylethyl ether and finally with a $C_4$-$C_8$ alkane or $C_5$-$C_8$ cycloalkane such pentane, hexane or cyclohexane.

In the acid addition salt of APIP with CAA obtained by the process B of the present invention the molar ratio of the APIP enantiomers (hereinafter also referred to as S/R or R/S value) is usually at least 90 to 10, corresponding to 80% ee, in particular at least 95:5, corresponding to 90% ee. However, optical purity can be further improved by recrystallization of said acid addition salt from a suitable solvent. Suitable solvents include but are not limited to water, $C_1$-$C_4$-alkanols, in particular methanol or ethanol, and mixtures thereof with water. By this recrystallization, the optical purity can be improved to an enantiomeric excess of the desired enantiomer of at least 95% ee, preferably at least 98% ee or even at least 99%. In order to achieve recrystallization it is not necessary to completely dissolve the acid addition salt. Likewise it is possible to stir a slurry of the salt in a suitable solvent for a prolonged period of time e.g. from 2 to 24 h, optionally applying a temperature gradient during stirring, starting with a higher temperature and ending with a lower temperature.

Both the fractional crystallization of the acid additions salt of APIP with CAA and the recrystallization of the acid additions salt of APIP with CAA may be carried out as a batch process or as a continuous process. One means for carrying out the process continuously is illustrated in FIG. 1 of WO 97/32644, to which full reference is made.

The thus obtained acid addition salt of an APIP enantiomer with CAA may be transformed into the free base according to well-known techniques, for example those described in the prior art cited in the introductory part of the present application, such as treating the APIP/CAA acid addition salt with diluted aqueous base and removing the CAA in its anionic form for instance by means of ion exchange resins. Preferably, however, the acid addition salt of an APIP enantiomer with CAA is converted into acid addition salt of the APIP enantiomer with a strong acid, such as hydrochloric acid. This is usually accomplished by initially suspending the APIP/CAA addition salt in an aqueous solvent, such as water or a mixture of water with a water-miscible organic solvent, and in particular water. The resulting suspension is treated with an aqueous solution of a strong mineral acid such as an aqueous hydrochloric acid or aqueous sulphuric acid, and in particular concentrated aqueous hydrochloric acid (about 37% by weight). Thereby, the acid addition salt of enantiomeric APIP with the chiral carboxylic acids A is transferred into the acid addition salt of APIP with said strong mineral acid which remains dissolved in the aqueous phase, while the chiral carboxylic acid A precipitates from the aqueous phase. The precipitated chiral carboxylic acid A is recovered by filtration, washing and drying, and is then available for reuse. The mother liquor is washed with a suitable organic solvent of relative high polarity, such as some of the solvents listed in the group 6 mentioned before, in particular 2-butanone, in order to remove traces of the chiral carboxylic acid A. The mother liquor is then filtered, e.g. over diatomaceous earth, and concentrated under reduced pressure and the obtained residue is optionally dried via one or two azeotropic distillations under reduced pressure after adding for example isopropanol or a mixture of methanol and isopropanol. The finally obtained product is the acid addition salt of an APIP enantiomer with said strong acid, and particular is a hydrochloride addition salt of an APIP enantiomer, which may be further purified, e.g. by recrystallization.

According to a preferred embodiment of the invention the acid addition salt of an APIP enantiomer, in particular (R)-APIP, with CAA is converted into enantiomeric APIP dihydrochloride monohydrate, in particular (R)-APIP dihydrochloride monohydrate, i.e. the addition salt of (R)- or (S)-APIP with hydrochloric acid which includes about 2 moles of hydrochloric acid and about 1 mol of water per mol of APIP.

In contrast to the known anhydrous APIP dihydrochloride the (R)- as well as (S)-APIP dihydrochloride monohydrate, and in particular (R)-APIP dihydrochloride monohydrate, have surprisingly been found to be highly crystalline compounds which can easily be further purified, e.g. via crystallization, in order to improve both their chemical and enantiomeric purity. (R)- and (S)-APIP dihydrochloride monohydrate crystallise in very large crystals generally >0.5 mm, (frequently a size of approx. 1-2 mm) that are easily filterable, have a very low tendency for hold-up of mother liquor and an increased stability and therefore feature improved storage and handling properties compared to the anhydrous (S)- or (R)-APIP dihydrochloride (hereinafter also termed (S)- or (R)-APIP dihydrochloride anhydrate).

The present invention therefore also relates to crystalline (R)-3-aminopiperidine-dihydrochloride-monohydrate and (S)-3-aminopiperidine-dihydrochloride-monohydrate. Both (R)- and (S)-3-aminopiperidine-dihydrochloride-monohydrate comprise about 2 moles, e.g. 1.90 to 2.10 moles and in particular 1.95 to 2.05 moles, of hydrochloride and about 1 mol, e.g. 0.9 to 1.1 moles and in particular 0.95 to 1.05 moles, of water.

Both (R)-3-aminopiperidine-dihydrochloride-monohydrate and (S)-3-aminopiperidine-dihydrochloride-monohydrate are characterized by a X-ray powder diffraction diagram, which, at 22° C. and using Cu-Kα radiation, displays at least 5, in particular at least 7, more particular at least 9 or at least 11, and especially all of the following reflections, quoted as 2θ values: 11.0±0.2°, 16.4±0.2°, 17.0±0.2°, 20.9±0.2°, 24.5±0.2°, 25.3±0.2°, 25.9±0.2°, 26.7±0.2°, 27.3±0.2°, 28.4±0.2°, 29.3±0.2°, 30.0±0.2°, 30.7±0.2°, 31.0±0.2° and 31.8±0.2°. Often at least one of the following reflections, in particular 1, 2 or 3 of following reflections will be observed: 17.0±0.2°, 20.9±0.2°, 24.5±0.2°, optionally together with 3 or more of the other reflections.

In contrast thereto, the known (R)-3-aminopiperidine-dihydrochloride-anhydrate and likewise the (R)-3-aminopiperidine-dihydrochloride-anhydrate are characterized by a X-ray powder diffraction diagram, which, at 22° C. and using Cu-Kα radiation, displays the following reflections, quoted as 2θ values: 9.0±0.2°, 15.8±0.2°, 17.9±0.2°, 19.7±0.2°, 21.7±0.2°, 23.1±0.2°, 24.4±0.2°, 25.3±0.2°, 28.9±0.2° and 30.7±0.2°.

(R)-3-aminopiperidine-dihydrochloride-monohydrate shows a specific rotation of >−1.5 in particular-1,7 (20° C., concentration C=10 in $H_2O$ and 589 nm), ee>98% (HPLC)

The water content in the (R)-3-aminopiperidine-dihydrochloride-monohydrate was determined to be 9% (Karl-Fischer Titration). That corresponds to 1 mol of water per mol of APIP.

In the NIR spectra (near infrared spectra) of the (R)-3-aminopiperidine-dihydrochloride-monohydrate the typical signals of a hydrate are present, in particular a strong band at 5070 $cm^{-1}$. (see FIG. 1)

The melting point for (R)-3-aminopiperidine-dihydrochloride-monohydrate is 204-207° C. That is almost identical to that of the anhydrous (R)-3-aminopiperidine-dihydrochloride as the water is removed during heating.

As pointed out above, the diastereomeric acid addition salts of APIP with CAA, in particular the acid addition salts of (R)-APIP with a carboxylic acids A-1 and the acid addition salts of (S)-APIP with a carboxylic acids A-2, are of high optical purity with regard to the enantiomers of APIP, the enantiomeric excess (% ee.) being generally at least 70% ee, frequently 80% ee, preferably at least 90% ee, in particular at least 95% ee, more preferably at least 98% ee or at least 99% ee or at least 99.5% ee. These diastereomeric acid addition salts of APIP with CAA are novel and are also part of the invention.

In these salts the molar ratio of APIP to CAA is close to stoichiometry, but small deviations are possible. Usually the molar ratio of APIP to CAA in these salts is from 0.9:2 to 1.1:2, in particular from 0.95:2 to 1.05:2.

The diastereomeric acid addition salts of APIP with CAA may be present in pure form, i.e. the impurities different from APIP and CAA make up at most 1% by weight, in particular at most 0.5% by weight or at most 0.1% by weight of the total weight of the acid addition salt. However, the diastereomeric acid addition salts of APIP with CAA may be present in the form of solvates, e.g. hydrates, which are also part of the present invention. In particular, the diastereomeric acid addition salts of APIP with CAA are present in the form of solvates with water. The solvates might be beneficial with regard to formation of crystalline material. Thus, a preferred embodiment of the invention relates to diastereomeric acid addition salts of APIP with CAA in the form of solvates with water. According to a more preferred embodiment of the invention the diastereomeric acid addition salts of (R)-APIP with carboxylic acids A-1 comprise about 1 mol, e.g. 0.95 to 1.05 moles and in particular 0.98 to 1.02 moles, of water per mol of APIP, and the diastereomeric acid addition salts of (S)-APIP with carboxylic acids A-2 comprise about 2 moles, e.g. 1.90 to 2.10 moles and in particular 1.95 to 2.05 moles, of water per mol of APIP.

Thus, particularly preferred embodiments of the present invention relate to the following acid addition salts:
(R)-APIP (S)-2-(4-methylphenyl)sulfonylamino-hydropropionate (1:2) monohydrate,
(R)-APIP (S)-2-(4-chlorophenyl)sulfonylamino-hydropropionate (1:2) monohydrate,
(R)-APIP (S)-2-(phenyl)sulfonylamino-hydropropionate (1:2) monohydrate,
(S)-APIP (S)-2-(3-phenylureido)-hydropropionate (1:2) dihydrate, and
(S)-APIP (S)-2-(3-(4-chlorophenyl)ureido)-hydropropionate (1:2) dihydrate.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

The following examples shall serve the further illustration of the invention and are not intended to limit the scope of the present invention.

ABBREVIATIONS

Figure 1:
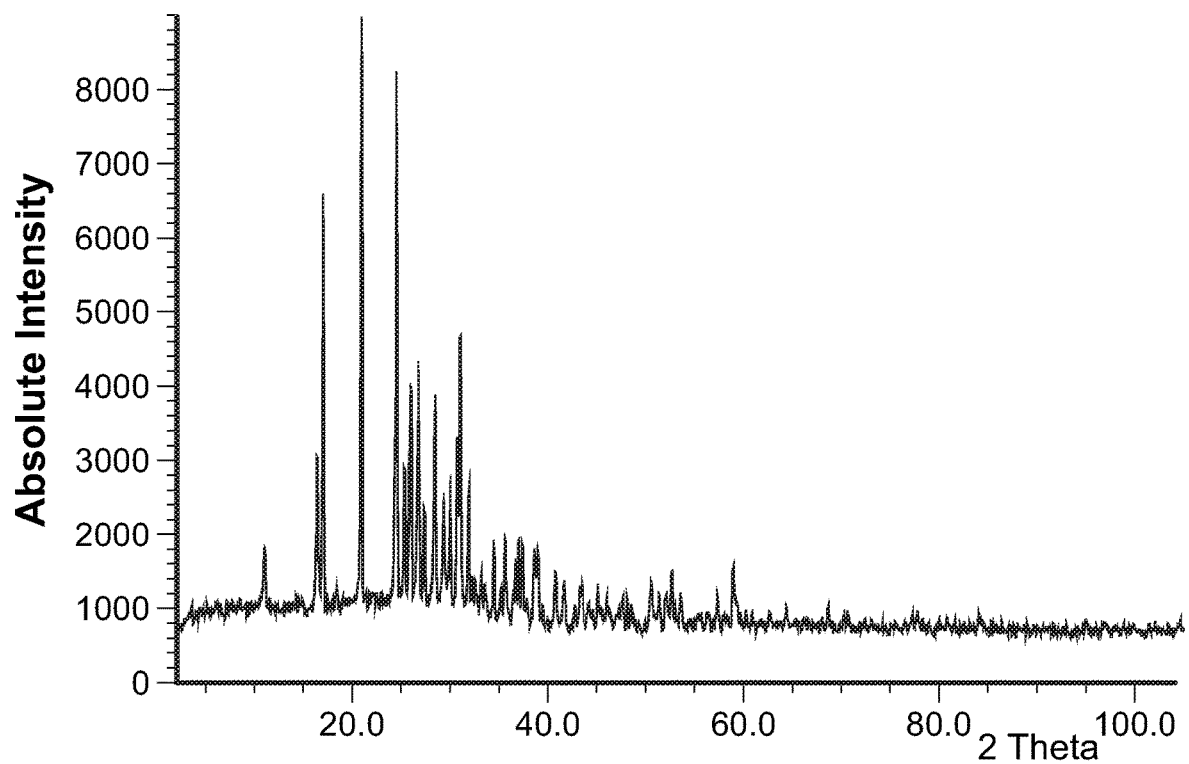
FIG. 1 shows the powder X-ray diffraction pattern of (R)-aminopiperidine dihydrochloride monohydrate obtained from example 5.

Ts-L-Ala: (S)-2-(4-methylphenyl)sulfonylamino-propionic acid
pCl-Ps-L-Ala (S)-2-(4-chlorophenyl)sulfonylamino-propionic acid
Ps-L-Ala: (S)-2-phenyl sulfonylamino-propionic acid
PC-L-Ala: (S)-2-(3-phenylureido)-propionic acid
Cl-PC-L-Ala: (S)-2-(3-(4-chlorophenyl)ureido)-propionic acid
rac-APIP: racemic 3-aminopiperidine
(R)-APIP: (R)-3-aminopiperidine
(S)-APIP: (S)-3-aminopiperidine
S/R: enantiomeric ratio of (S)-APIP/(R)-APIP
TBME: tert.-butylmethyl ether
MeOH: methanol
MEK: methyl ethyl ketone (2-butanone)
r.t.: room temperature (22° C.)
conc.: concentrated
Analytics:
The enantiomeric ratio S/R was measured via chiral HPLC after derivatisation with mosher's acid chloride on a Chiralpak AD 250/4.6/10 column with hexane/isopropanol 90:10 as eluent. The detection wavelength was 220 nm. The retention times were: Rt(R-APIP)=8 min and Rt (S-APIP)= 14 min, respectively.

Measurements of powder X-ray diffraction patterns were performed at room temperature (22° C.) on a powder diffractometer STOE STADI P using Cu-K$\alpha_1$ radiation (1.540598 Å) in Debeye Scherrer geometry. Samples were contained in capillaries having an internal diameter of about 0.3 mm.

I Preparation of APIP

Example 1: Preparation of Piperidine-3-Carboxylic Acid Hydrazide (Nipecotic Acid Hydrazide)

157 g racemic ethyl nipecotate and 53 g hydrazine hydrate were stirred overnight at 80° C. The solution was cooled to r.t, and gradually diluted with 280 g TBME. The resulting suspension was stirred for one hour. Racemic nipecotic acid hydrazide (123 g) was isolated via filtration under suction and drying at 50° C. as white crystalline solid. Melting point: 111° C.

Example 2: Preparation of Piperidine-3-Carboxylic Acid Hydrazide (Nipecotic Acid Hydrazide) Monohydrochloride 157 g racemic ethyl nipecotate (technical grade, 1.0 mol) and 55.1 g hydrazine hydrate (1.1 mmol) were stirred overnight at 80° C. The solution was diluted with 100 g distilled water and cooled to r.t. Then 99 g of conc. hydrochloric acid (1.0 mol) were slowly added, and the suspension was stirred overnight. The precipitated crystals were filtered and washed with cold water (2×10 ml), isopropanol (2×10 ml) and pentane (50 ml) to afford 119 g of racemic nipecotic acid hydrazide monohydrochloride. Additional 25.4 g could be obtained from the mother liquor via evaporation and recrystallization from water. Thus, a total of 144 g pure racemic nipecotic acid hydrazide monohydrochloride (80%) was isolated.

Melting point: 127° C.

Example 3: Preparation of (R)-APIP Dihydrochloride from R-Ethyl Nipecotate Tartric Acid Salt To a well stirred suspension of 153.6 g R-ethyl nipecotate L-tartaric acid salt in 157 g xylene (technical mixture) was added dropwise under cooling a solution of 69.3 g technical potassium hydroxide in 78 g water. The organic phase was separated; the water phase was extracted again respectively with 50 and 40 g xylene. The combined organic phase was dried over 10 g sodium sulfate. The drying agent was filtered off and 39 g hydrazine hydrate was added. The biphasic mixture was heated to 80° C. for 2 days under vigorous stirring. The mixture was concentrated under vacuum and the residue was taken up in water and was concentrated again to yield 168 g of a 40.6% solution of R-nipecotic acid hydrazide in water.

To this solution was added 50 g of cracked ice. The pH was adjusted with 77 g conc. hydrochloride acid to a value of 2.0. Approx. one fifth of this solution was set aside, and to the main part of the solution was added 1 ml conc. hydrochloride acid. Diazotation was carried out at <0° C. first with 18 g isopentyl nitrite, then the remaining nipecotic acid dihydrochloride solution, which had been put aside, was carefully added under cooling, and finally 53 g isopentyl nitrite were added dropwise at a temperature between −5 to −2° C. (about 200 g of cracked ice were added in portions to keep the mixture cold). Afterwards, the solution was stirred at 0° C. for one hour. The water phase was separated and poured during 20 min onto 100 g of boiling water. Boiling was continued for 10 min, 5 g of conc. hydrochloride acid was added and the solution was concentrated to a final volume of 330 g with an APIP content of 66.2 g (as dihydrochloride, yield is 76% over three steps) and a content of the side product nipecotic acid of 4.6 g. The solution was concentrated to a thick mass, which was taken up in 74 g of boiling methanol. On cooling, R-APIP×2 HCl crystallized as thick mass. APIP×2 HCl was isolated after dilution with 150 g acetone via filtration. After drying in vacuo, 56.9 g dry R-APIP×2 HCl was obtained.

Example 4: Preparation of (R)-APIP Dihydrochloride with Hexyl Nitrite

To 68.3 g of a solution of R-nipecotic acid hydrazide in water (assay 41.9%. 200 mmol) was added 70 g ice and 46.8 g conc. hydrochloric acid (475 mmol, 1.95 eq referring to the total amount of hydrazide). The clear solution was cooled to −10° C., and 33 g n-hexyl nitrite was added during 30 min under cooling (ice/salt bath). 17.1 g of a solution of R-nipecotic acid hydrazide in water (assay 41.9%. 50 mmol) was added during 10 min under cooling.

Afterwards, additionally 16 g n-hexyl nitrite was added during 20 min under cooling. The solution was stirred for one hour at −5° C., the water phase was separated and poured in portions onto 100 g of boiling water (>95° C.). The pH-value is now 1.9 (measured via pH-paper). 5 g of conc. hydrochloric acid was added and the solution was concentrated to a thick mass, which was taken up in 50 g of boiling methanol. Isopropanol (100 g) was added, and the solution was concentrated to a mass of approx. 70 g. The solution was seeded, and diluted with acetone (100 g). R-APIP×2 HCl (36 g, 83%) was isolated via filtration and drying in vacuo.

Example 5: Preparation of (R)-APIP Dihydrochloride

To a solution of 136 kg (R)-nipecotic acid hydrazide in 194 kg deionized water was added 274 kg ice and 219 kg conc. hydrochloric acid. The solution was cooled to 0° C. and 50 kg isopentylnitrite was slowly added at a temperature of □2 to +2° C. A solution of 14.6 kg (R)-nipecotic acid hydrazide in 18.4 kg water was added. The solution was cooled again to 0° C., and 117 kg isopentylnitrite was slowly added at a temperature of −2 to +2° C. Finally the solution was stirred for 30 min at 0° C. This clear solution was pumped in small portions (about 30 l) to 400 kg water at 90° C. After complete addition, the solution was heated at 90° C. for 30 min. The solution was cooled to r.t. and the phases were separated.

To three combined water phases obtained this way from a total of 544 kg (R)-nipecotic acid hydrazide was added 200 kg conc. hydrochloric acid. The solution was concentrated to a thick syrup and dissolved in hot methanol (1300 kg). The solution was cooled to r.t., seeded with (R)-aminopiperidine dihydrochloride hydrate and diluted gradually with 900 kg acetone. The resulting crystals of (R)-aminopiperidine dihydrochloride monohydrate were isolated via centrifugation (601 kg wet; water content: 9% (Karl-Fischer-Titration)).

The powder X-ray diffraction pattern of the sample is shown in FIG. 1. The characteristic reflections are quoted in the following table as 2θ values or as interplanar spacings D together with relative intensities:

| 2θ | D [Å] | I rel [%] |
|---|---|---|
| 11.0 | 8.1 | 20 |
| 16.4 | 5.4 | 34 |
| 17.0 | 5.2 | 73 |
| 20.9 | 4.2 | 100 |
| 24.5 | 3.6 | 92 |
| 25.3 | 3.5 | 32 |
| 25.9 | 3.4 | 44 |
| 26.7 | 3.3 | 48 |
| 27.3 | 3.3 | 26 |
| 28.4 | 3.1 | 42 |
| 29.3 | 3.0 | 27 |
| 30.0 | 3.0 | 31 |
| 30.7 | 2.9 | 36 |
| 31.0 | 2.9 | 53 |
| 31.8 | 2.8 | 29 |

Figure 2:
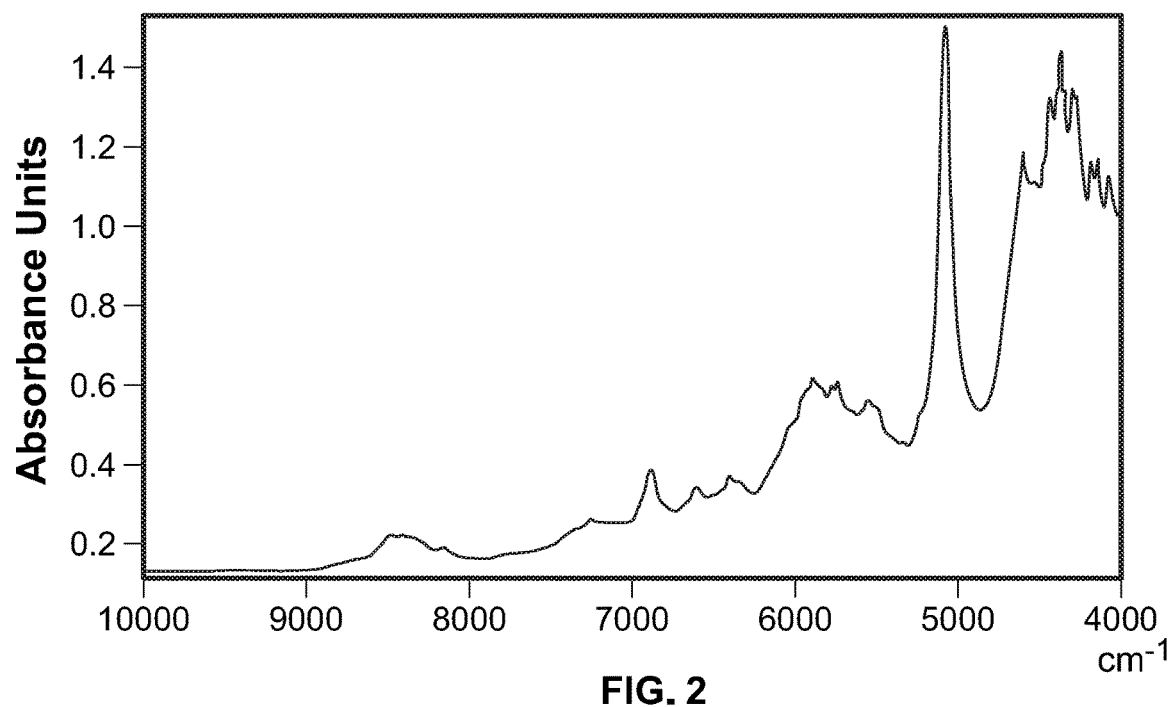
FIG. 2 shows the NIR spectrum of of (R)-aminopiperidine dihydrochloride monohydrate obtained from example 5.
Figure 3:
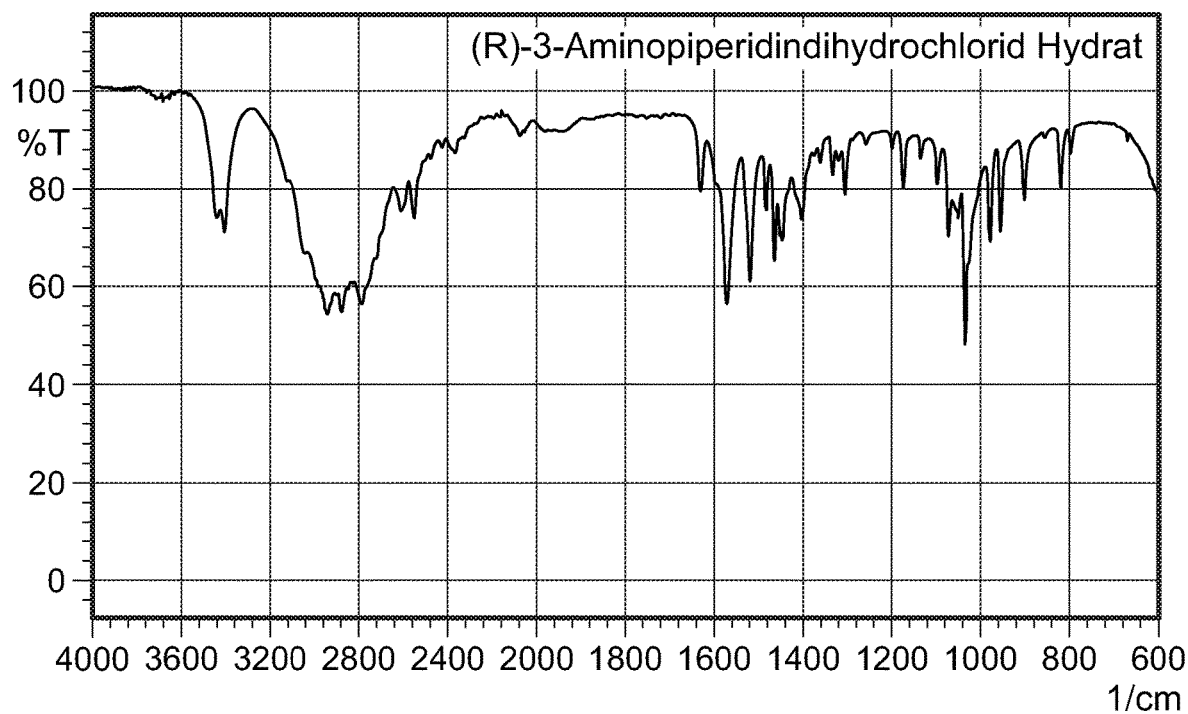
FIG. 3 shows the IR spectrum of of (R)-aminopiperidine dihydrochloride monohydrate obtained from example 5.

The NIR-spectrum of (R)-aminopiperidine dihydrochloride monohydrate is shown in FIG. 2. The IR spectrum of (R)-aminopiperidine dihydrochloride monohydrate is shown in FIG. 3.

To this solid was added methanol (400 kg) and isopropanol (1000 kg). The solvent was distilled under reduced pressure until a water content <1.0% was measured. The suspension was first diluted with methanol (400 kg) and then gradually with acetone (800 kg). The resulting solid was isolated via centrifugation (563 kg wet) and dried at elevated temperatures under reduced pressure to afford 522 kg chemically pure (R)-aminopiperidine dihydrochloride in the form of its anhydrate with an optical purity of >99 ee.

Figure 4:
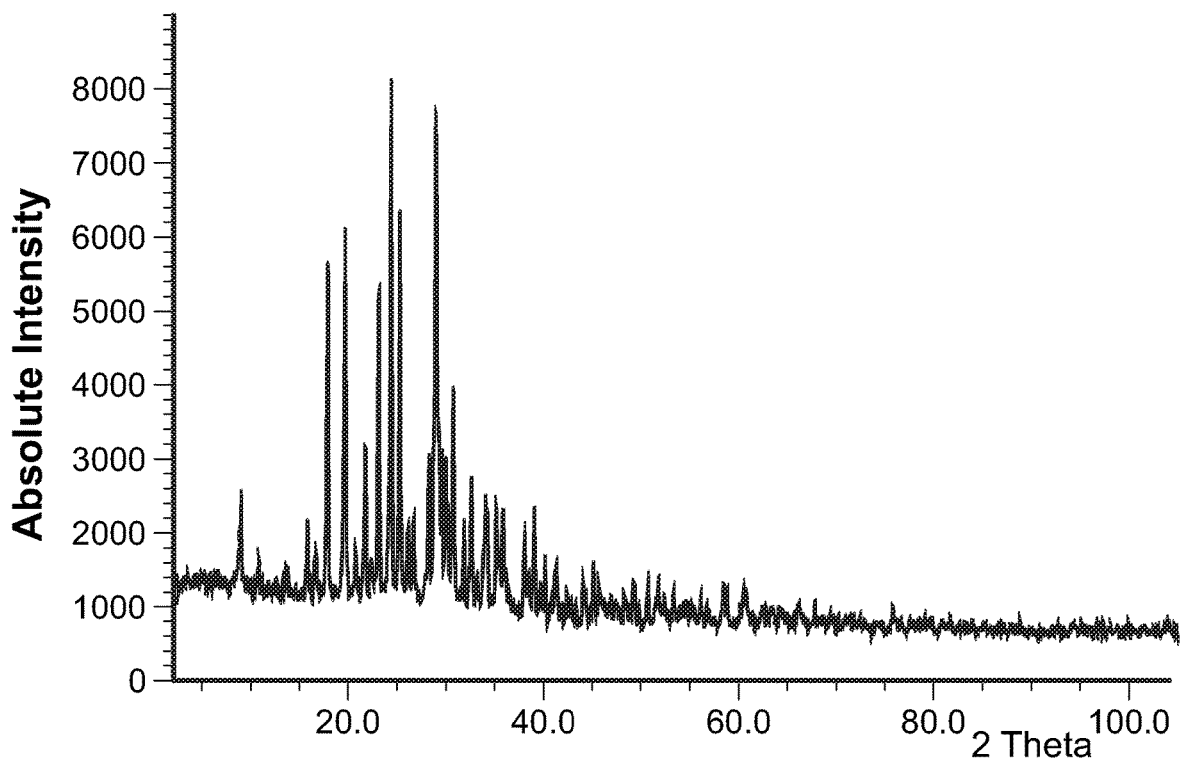
FIG. 4 shows the powder X-ray diffraction pattern of (R)-aminopiperidine dihydrochloride anhydrate obtained from example 5.

The powder X-ray diffraction pattern of the sample is shown in FIG. 4. The characteristic reflections are quoted in the following table as 2θ values or as interplanar spacings D together with relative intensities:

| 2θ | D [Å] | I rel [%] |
|---|---|---|
| 9.0 | 9.8 | 30 |
| 15.8 | 5.6 | 27 |
| 17.9 | 4.9 | 70 |
| 19.7 | 4.5 | 75 |
| 21.7 | 4.1 | 39 |
| 23.1 | 3.8 | 64 |
| 24.4 | 3.6 | 100 |
| 25.3 | 3.5 | 78 |
| 28.9 | 3.1 | 95 |
| 30.7 | 2.9 | 49 |

Example 6: Preparation of Rac-APIP Dihydrochloride with Isopentyl Nitrite

To 36 g (250 mmol) of racemic nipecotic acid hydrazide in 125 ml water were added 45 ml (500 mmol) of conc. hydrochloric acid under cooling (ice/salt). 25.1 g isopentyl nitrite (300 mmol) was added during 30 min at 0° C. and stirred at the same temperature for additional 30 min. HPLC shows complete conversion to the desired azide with no starting material left. The mixture was poured drop wise during 10 min onto 500 ml of hot (80° C.) water. Boiling was continued for additional 60 min. The solution was cooled to room temperature, conc. hydrochloric acid (40 ml) was added and the solution was concentrated to a viscous mass. Water (100 ml) was added, and the solution was concentrated again. Isopropyl alcohol (100 ml) was added, and the solution was concentrated again. The residue was dissolved in hot methanol (50 ml). To the cooled methanol solution was added acetone (100 g) dropwise under vigorous stirring.

The precipitated 3-aminopiperidine dihydrochloride was isolated (40 g of wet product) and dried via azeotropic distillation under reduced pressure with two portions (50 ml each) of isopropanol. Hot methanol was added and the suspension was stirred over night at r.t. The suspension was diluted with 70 g acetone and the solid material was isolated via filtration. 33.2 g (192 mmol, corresponds to 77% yield) of 3-aminopiperidine dihydrochloride was obtained as a white powder. Chemical purity (HPLC) is 98.7% with a water content (determined by Karl Fischer titration) of 0.046%.

Example 7: Preparation of Rac-APIP Dihydrochloride with Acetic Acid as Cosolvens To 5.40 g of racemic nipecotic acid hydrazide dihydrochloride (25 mmol) in 10 g water and 2.5 g acetic acid were added dropwise 3.5 g isopentyl nitrite (30 mmol) at □15° C. The clear solution was warmed to 0° C. during a period of 2 h and poured at once into 50 ml of boiling water. Boiling was continued for additional 10 min. The solution was cooled to r.t., conc. hydrochloride acid (2 ml) was added and the solution was concentrated to a viscous mass, which was dissolved in 10 ml of hot methanol. On cooling the clear solution to r.t. a thick crystalline mass developed. Acetone (20 ml) was added and the crystals were isolated via filtration. After drying for 12 h at 50° C., 3.71 g of racemic 3-aminopiperidine dihydrochloride (21 mmol, corresponds to 84% yield) with a water content of 0.68% were obtained.

Example 8: Preparation of Rac-APIP Dihydrochloride with Isopropanol as Cosolvens To 5.40 g of racemic nipecotic acid hydrazide dihydrochloride (25 mmol) in 5 g water and 5 g isopropanol were added dropwise 3.5 g isopentyl nitrite (30 mmol) at □15° C. The clear viscous solution was warmed to 0° C. during a period of 1 h and poured at once into 50 ml of boiling water. Boiling was continued for additional 10 min. The solution was cooled to r.t., conc. hydrochloride acid (2 ml) was added and the solution was concentrated to a viscous mass, which was dissolved in 10 ml hot methanol. On cooling the clear solution to r.t. a thick crystalline mass developed. Acetone (20 ml) was added and the crystals were isolated via filtration. After drying for 12 h at 50° C., 3.42 g of racemic 3-aminopiperidine dihydrochloride (20 mmol, corresponds to 80% yield) with a water content of 0.64% were obtained.

Example 9: Preparation of Racemic APIP Dihydrochloride with Sodium Nitrite 18 g of racemic nipecotic acid hydrazide monohydrochloride (100 mmol) were dissolved in 36 g water and 21 g of 37% hydrochloric acid (210 mmol) and cooled to □10° C. To the solution were added 7.6 g of $NaNO_2$ (110 mmol) in small portions in such a way that the temperature is kept ≤□5° C. Stirring was continued for 30 min at a temperature of □5 to 0° C. The cold solution was then poured in small portions into 20 g of boiling water. The reaction mixture was stirred under reflux for additional 30 min and then cooled— to r.t. to give a solution of racemic APIP dihydrochloride in water.

II Enantiomeric Resolution of Racemic APIP by Fractional Crystallization of Diastereomeric Acid Addition Salts

Example 10: Resolution of Rac-APIP with Ts-L-Ala

The solution of rac-APIP dihydrochloride obtained in Example 9 was diluted with 50 g distilled water, and then 100 ml of a 2N aqueous solution of sodium hydroxide (200 mmol) were added dropwise on an ice-water bath so that the pH-value is adjusted to 12. Afterwards 44 g of N-(para-toluenesulfonyl)-L-alanine (180 mmol) were added and the suspension was heated to 90° C. for 30 min to afford a clear solution. This solution was then cooled to 60° C. The precipitated crystals were aged at this temperature for 1 h and then stirred at r.t. overnight. The obtained salt was collected by filtration, washed with 10 ml isopropanol, 2×10 ml pentane and dried to give 31.35 g of (R)-APIP·2 Ts-L-Ala·$H_2O$ as white solid. Yield: 52% (based on the amount of rac-APIP used).

Enantiomeric ratio S/R=9.57:90.43.

The obtained acid addition salt was purified by recrystallization from 210 g of water, Yield: 18.62 g, 31% (based on the amount of rac-APIP used).

Enantiomeric ratio S/R=0.2:99.8.

Example 11: Resolution of Rac-APIP with Ts-L-Ala

A solution of 400 mg (10 mmol) sodium hydroxide in 5.0 g water were added dropwise to a solution of 865 mg (5 mmol) rac-APIP dihydrochloride in 5.0 g water and the mixture was stirred for 10 min. 2428 mg (10 mmol) Ts-L-Ala were added and the mixture was heated at 80° C. until a clear solutions was obtained. The solution was cooled slowly to r.t. and the suspension was stirred for 3 h. The formed solid was collected by filtration, washed with mother liquor, water, isobutanol, TBME and pentane (1 ml each) and dried to afford (R)-APIP·2 Ts-L-Ala·$H_2O$.

Yield: 1435 mg, 95% (based on the amount of enantiomer used).

Enantiomeric ratio S/R=2.06:97.94; S-factor (efficiency of optical resolution)=0.91.

The obtained acid addition salt was purified by recrystallization from 13.0 g water.

Yield: 1087 mg, 72% (based on the amount of enantiomer used).

Enantiomeric ratio S/R=0.0:100.0.

Melting point: 152° C.

Specific rotation $[\alpha]_D^{20}$=−3.8 (c=0.5, MeOH).

Example 12: Resolution of Rac-APIP with Ts-L-Ala 400 mg (10 mmol) sodium hydroxide in 5.0 g water and 300 mg (5 mmol) acetic acid were added subsequently to a suspension of 865 mg (5 mmol) rac-APIP dihydrochloride in 5.0 g water and stirred for 10 min. 1460 mg (6 mmol) Ts-L-Ala were added and the mixture was heated at 80° C. until a clear solution was obtained. The solution was cooled slowly to r.t. and the suspension was stirred for 3 h. The solid was collected by filtration, washed with mother liquor, water, isobutanol, TBME and pentane (1 ml each) and dried to afford (R)-APIP·2 Ts-L-Ala·$H_2O$.

Yield: 1265 mg, 84% (based on the amount of enantiomer used).

Enantiomeric ratio S/R=2.0:98.0.

The obtained acid addition salt was purified by recrystallization from 12.0 g of water.

Yield: 858 mg, 57% (based on the amount of enantiomer used).

Enantiomeric ratio S/R=0.0:100.0.

Example 13: Resolution of Rac-APIP with pCl-Ps-L-Ala 80 mg (2 mmol) sodium hydroxide in 1.0 g water were added dropwise to a solution of 173 mg (1 mmol) rac-APIP dihydrochloride in 1.0 g water and the mixture was stirred for 10 min. 527 mg (2 mmol) pCl-Ps-L-Ala was added and the mixture was heated at 40° C. for 30 min. The solution was cooled slowly to r.t. and the suspension was stirred for 2 h. The formed solid was collected by filtration, washed with mother liquor, water (2×0.5 ml), acetone (1 ml), and pentane (2 ml) and dried to afford (R)-APIP·2 pCl-Ps-L-Ala·H$_2$O.

Yield: 273 mg, 85% (based on the amount of enantiomer used).

Enantiomeric ratio S/R=4.41:95.59; S-factor (efficiency of optical resolution)=0.77.

A pure acid addition salt was independently prepared from 5 mmol (R)-APIP·2HCl, 10 mmol NaOH and 10 mmol pCl-Ps-L-Ala in 10 g water which had an optical purity of 100% and shows the following physical data:

Enantiomeric ratio S/R=0.0:100.0.

Melting point: 139° C.

Specific rotation $[\alpha]_D^{20}$=−0.3 (c=1.0, MeOH).

Example 14: Resolution of Rac-APIP with Ps-L-Ala 400 mg (10 mmol) sodium hydroxide in 5.0 g water were added dropwise to a solution of 865 mg (5 mmol) rac-APIP dihydrochloride in 5.0 g water and the mixture was stirred for 10 min. 2293 mg (10 mmol) of Ps-L-Ala were added and the mixture was heated at 80° C. until a clear solutions was obtained. The solution was cooled slowly to r.t. and the suspension was stirred for 3 h. The formed solid was collected by filtration, washed with mother liquor, water, isobutanol, TBME and pentane (1 ml each) and dried to afford (R)-APIP·2 Ps-L-Ala·H$_2$O as white solid. Yield: 765 mg, 53% (based on the amount of enantiomer used).

Enantiomeric ratio S/R=2.99:97.01.

Example 15: Resolution of Rac-APIP with Ps-L-Ala 400 mg (10 mmol) sodium hydroxide in 5.0 g water and 300 mg (5 mmol) acetic acid were added dropwise to a solution of 865 mg (5 mmol) rac-APIP dihydrochloride in 5.0 g water and the mixture was stirred for 10 min. 1146 mg (5 mmol) of Ps-L-Ala were added and the mixture was heated at 80° C. until a clear solutions was obtained. The solution was cooled slowly to r.t. and the suspension was stirred for 3 h. The formed solid was collected by filtration, washed with mother liquor, water, isobutanol, TBME and pentane (1 ml each) and dried to afford (R)-APIP·2 Ps-L-Ala·H$_2$O as white solid.

Yield: 1069 mg, 74% (based on the amount of enantiomer used).

Enantiomeric ratio S/R=3.71:96.29.

The obtained acid addition salt was purified by recrystallization from 6.0 g of water. Yield: 605 mg, 42% (based on the amount of enantiomer used).

Enantiomeric ratio S/R=0.03:99.97.

Melting point: 180.6° C.

Specific rotation $[\alpha]_D^{20}$=−4.4 (c=0.5, MeOH).

Example 16: Resolution of Rac-APIP with PC-L-Ala 400 mg (10 mmol) sodium hydroxide in 5.0 g water were added dropwise to a solution of 865 mg (5 mmol) rac-APIP dihydrochloride in 5.0 g water and the mixture was stirred for 10 min. 2082 mg (10 mmol) of PC-L-Ala were added and the mixture was heated at 80° C. until a clear solution—was obtained. The solution was cooled slowly to r.t. and the suspension was stirred for 3 h. The formed solid was collected by filtration, washed with mother liquor, water, isobutanol, TBME and pentane (1 ml each) and dried to afford (S)-APIP·2 PC-L-Ala·2H$_2$O as white solid.

Yield: 1220 mg, 88% (based on the amount of enantiomer used).

Enantiomeric ratio S/R=98.88:1.12. S-factor (efficiency of optical resolution)=0.86.

1000 mg of the obtained acid addition salt was purified by recrystallization from 6.0 g of water.

Yield: 504 mg.

Enantiomeric ratio S/R=99.93:0.07.

Melting point: 135.2° C.

Specific rotation $[\alpha]_D^{20}$=+3.4 (c=0.5, MeOH).

Example 17: Resolution of Rac-APIP with Cl-PC-L-Ala

A mixture of 100 mg (1 mmol) rac-APIP and 246 mg (1 mmol) (S)-2-(3-(4-chlorophenyl)ureido)-propionic acid in 1000 mg ethanol was homogenized at 70° C., cooled down to r.t., diluted with 1 ml isopropanol and stirred for 1 h. The solids were filtered off, washed with mother liquor, isopropanol, TBME and pentane (1 ml each) and dried to afford (S)-APIP·2 Cl-PC-L-Ala·2H$_2$O.

Yield: 209 mg, 67% (based on the amount of enantiomer used).

Enantiomeric ratio S/R=96.74:3.26.

Example 18: Resolution of Rac-APIP with Cl-PC-L-Ala

A mixture of 350 mg (3.5 mmol) rac-APIP and 1723 mg (7 mmol (S)-2-(3-(4-chlorophenyl)ureido)-propionic acid in 7000 mg of aqueous ethanol (50% (v/v)) was homogenized at 70° C. and cooled down to 40° C. thereby obtaining a precipitation. The suspension was stirred at this temperature for 1 h and then at r.t. for another 1 h. The solid was collected by filtration, washed with mother liquor, isopropanol, TBME and pentane, (1 ml each) and dried to afford (S)-APIP·2 L-p-Chlor-PC-Ala·2H$_2$O.

Yield: 1025 mg, 93% (based on the amount of enantiomer used).

Enantiomeric ratio S/R=90.04:9.96.

The obtained acid addition salt was purified by stirring in 5.0 g of aqueous ethanol (50% (v/v)) at 70° C., then at r.t.

Yield: 858 mg, 78% (based on the amount of enantiomer used).

Enantiomeric ratio S/R=99.7:0.3.

Melting point: 138°.

Specific rotation $[\alpha]_D^{20}$=+3.2 (c=0.5, MeOH)

III Conversion of Diastereomeric Acid Addition Salt of (R)-APIP with a Chiral Acid into (R)-APIP Dihydrochloride Monohydrate ((R)-APIP·2 HCl·H₂O)

Example 19: Conversion of (R)-APIP·2 Ts-L-Ala·H₂O into (R)-APIP·2 HCl·H₂O 18.6 g (31 mmol) of (R)-APIP·2 Ts-L-Ala·H₂O (from Example 10) were suspended in 80 g water, cooled with an ice-water bath and treated with 15.3 g (155 mmol) conc. hydrochloric acid. The precipitated Ts-L-Ala was collected by filtration, washed with 3×10 ml water and dried to obtain 13.93 g (57 mmol; 92% yield) of recovered Ts-L-Ala. The mother liqueur was washed with 2×50 ml MEK to remove last traces of Ts-L-Ala, filtered over celite and evaporated. The resulting yellow oil was dissolved in 20 g methanol, diluted with 20 g isopropanol and evaporated to dryness. This procedure was repeated once again to afford 6.42 g (R)-APIP·2HCl·H₂O with an APIP (free base) content of 53.6% by weight and a water content of 4.2%. (Thus a mixture of the hydrate and the anhydrous APIP was obtained in this case).

Yield: 31% (based on the amount of racemate used).

Combined mother liqueurs from salt formation and purification were evaporated to dryness and dissolved in 160 g of water. 27.6 g (280 mmol) conc. hydrochloric acid was added dropwise under ice cooling so that the pH-value is adjusted to 1. The solid was filtered off and dried to obtain 24.45 g (101 mmol) of recovered Ts-L-Ala.

Total yield of recovered Ts-L-Ala: 38.38 g (158 mmol), 88% (based on the total amount used).

We claim:

1. A process for enantiomeric enrichment of 3-aminopiperidine with regard to its R-enantiomer, the process comprising the fractional crystallization of 3-aminopiperidine in the form of its acid-addition salt with a chiral carboxylic acid A from a solution, suspension or emulsion containing a mixture of the enantiomers of 3-aminopiperidine, where the chiral carboxylic acid A is a compound of the formula A,

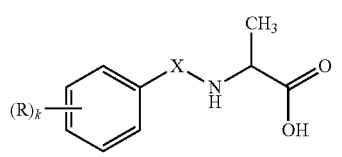

(A)

wherein k is 0, 1, 2, 3, 4 or 5, R is $C_1$-$C_2$-alkyl, $C_1$-$C_2$-alkoxy or halogen, and X is $S(O)_2$, C(O) or NHC(O), where the chiral carboxylic acid A has an enantiomeric excess with regard to one of its enantiomers.

2. The process according to claim 1, wherein the carboxylic acid A is selected from (S)-2-phenylsulfonylamino-propionic acid, (S)-2-(4-methylphenyl)sulfonylamino-propionic acid, (S)-2-(4-chlorophenyl)sulfonylamino-propionic acid, (R)-2-(3-phenylureido)-propionic acid and (R)-2-(3-(4-chlorophenyl)ureido)-propionic acid.

3. The process of claim 1, wherein the mixture of the enantiomers of 3-aminopiperidine is a racemic mixture of the enantiomers of 3-aminopiperidine.

4. The process of claim 1, wherein k is 0, 1, 2 or 3.

5. A process for enantiomeric enrichment of 3-aminopiperidine with regard to its S-enantiomer, the process comprising the fractional crystallization of 3-aminopiperidine in the form of its acid-addition salt with a chiral carboxylic acid A from a solution, suspension or emulsion containing a mixture of the enantiomers of 3-aminopiperidine, where the chiral carboxylic acid A is the compound of the formula A,

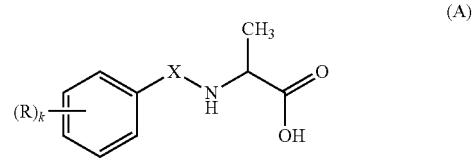

(A)

wherein k is 0, 1, 2, 3, 4 or 5, R is $C_1$-$C_2$-alkyl, $C_1$-$C_2$-alkoxy or halogen, and X is $S(O)_2$, C(O) or NHC(O), where the chiral carboxylic acid A has an enantiomeric excess with regard to one of its enantiomers.

6. The process according to claim 5, wherein the carboxylic acid A is selected from (R)-2-phenyl sulfonylamino-propionic acid, (R)-2-(4-methylphenyl)sulfonylamino-propionic acid, (R)-2-(4-chlorophenyl)sulfonylamino-propionic acid, (S)-2-(3-phenylureido)-propionic acid and (S)-2-(3-(4-chlorophenyl)ureido)-propionic acid.

7. The process of claim 5, wherein the mixture of the enantiomers of 3-aminopiperidine is a racemic mixture of the enantiomers of 3-aminopiperidine.

8. The process of claim 5, wherein k is 0, 1, 2 or 3.

9. A process for enantiomeric enrichment of 3-aminopiperidine with regard to its R-enantiomer, the process comprising the fractional crystallization of 3-aminopiperidine in the form of its acid-addition salt with a chiral carboxylic acid A from a solution, suspension or emulsion containing a mixture of the enantiomers of 3-aminopiperidine, where the chiral carboxylic acid A is the compound of the formula A,

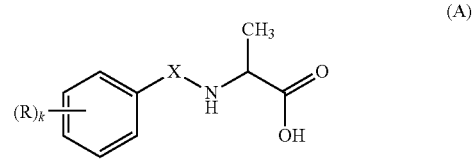

(A)

wherein k is 0, 1, 2, 3, 4 or 5, R is CN, $NO_2$, $C_1$-$C_2$-alkyl, $C_1$-$C_2$-alkoxy or halogen, or two adjacent variables R may together represent an optionally substituted butadien-1,4-diyl, and X is $S(O)_2$ or NHC(O), where the chiral carboxylic acid A has an enantiomeric excess with regard to one of its enantiomers.

10. The process of claim 9, wherein the mixture of the enantiomers of 3-aminopiperidine is a racemic mixture of the enantiomers of 3-aminopiperidine.

11. A process for enantiomeric enrichment of 3-aminopiperidine with regard to its S-enantiomer, the process comprising the fractional crystallization of 3-aminopiperidine in the form of its acid-addition salt with a chiral carboxylic acid A from a solution, suspension or emulsion containing a mixture of the enantiomers of 3-aminopiperidine, where the chiral carboxylic acid A is the compound of the formula A,

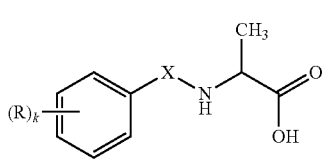

wherein k is 0, 1, 2, 3, 4 or 5, R is CN, NO$_2$, C$_1$-C$_2$-alkyl, C$_1$-C$_2$-alkoxy or halogen, or two adjacent variables R may together represent an optionally substituted butadien-1,4-diyl, and X is S(O)$_2$ or NHC(O), where the chiral carboxylic acid A has an enantiomeric excess with regard to one of its enantiomers.

12. The process of claim 11, wherein the mixture of the enantiomers of 3-aminopiperidine is a racemic mixture of the enantiomers of 3-aminopiperidine.

13. The acid-addition salt of 3-aminopiperidine with the chiral carboxylic acid A,

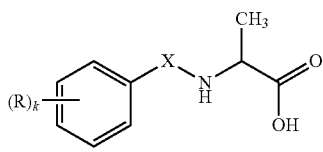

and the hydrates thereof,
wherein k is 0, 1, 2, 3, 4 or 5, R is C$_1$-C$_2$-alkyl, C$_1$-C$_2$-alkoxy or halogen, and X is S(O)$_2$, C(O) or NHC(O).

14. The acid-addition salt of claim 13, which has an enantiomeric excess with regard to one of the enantiomers of 3-aminopiperidine of at least 70%.

15. The acid-addition salt of claim 13, wherein k is 0, 1, 2 or 3.

16. The acid-addition salt of 3-aminopiperidine with the chiral carboxylic acid A,

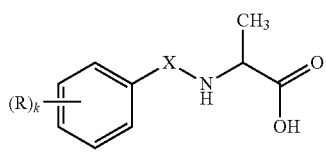

and the hydrates thereof,
wherein k is 0, 1, 2, 3, 4 or 5, R is CN, NO$_2$, C$_1$-C$_2$-alkyl, C$_1$-C$_2$-alkoxy or halogen, or two adjacent variables R may together represent an optionally substituted butadien-1,4-diyl, and X is S(O)$_2$ or NHC(O).

17. The acid-addition salt of claim 16, which has an enantiomeric excess with regard to one of the enantiomers of 3-aminopiperidine of at least 70%.

* * * * *